United States Patent [19]

Kondo et al.

[11] Patent Number: 5,166,203
[45] Date of Patent: Nov. 24, 1992

[54] QUINOLINECARBOXYLIC ACID DERIVATIVES, ANTIBACTERIAL AGENT CONTAINING THE SAME

[75] Inventors: Hirosata Kondo, Suita; Masahiro Taguchi, Hirakata; Yoshikazu Jinbo, Osaka; Yoshimasa Inoue, Osaka; Yasuo Kotera, Osaka; Fumio Sakamoto, Daito, all of Japan

[73] Assignee: Kanebo, Ltd., Tokyo, Japan

[21] Appl. No.: 703,739

[22] Filed: May 12, 1991

[30] Foreign Application Priority Data

Aug. 30, 1990 [JP] Japan .................................. 2-229651

[51] Int. Cl.$^5$ ................. C07D 413/04; A61K 31/535
[52] U.S. Cl. .................. 514/230.5; 514/233.2; 544/105; 544/115
[58] Field of Search ........................ 544/105, 115, 343; 514/250, 230.5, 233.2

[56] References Cited

U.S. PATENT DOCUMENTS

| 4,382,892 | 5/1983 | Hayakawa et al. | 544/101 |
| 4,808,584 | 2/1989 | Taguchi et al. | 514/279.5 |
| 4,853,469 | 8/1989 | Taguchi et al. | 544/99 |
| 4,971,967 | 11/1990 | Kondo et al. | 514/233.2 |

FOREIGN PATENT DOCUMENTS 286089 10/1988 European Pat. Off. .
387877 9/1990 European Pat. Off. .

OTHER PUBLICATIONS

Kondo et al, Chemical Abstracts, vol. 114, entry 10205(g) (1991).
Proceedings of the 109th Annual Meetings of the Pharmaceutical Society of Japan, Nagoya 1989, vol. IV, p. 30 with English translation.

Primary Examiner—John M. Ford
Attorney, Agent, or Firm—Wegner, Cantor, Mueller & Player

[57] ABSTRACT

Novel quinolinecarboxylic acid derivatives of the formula:

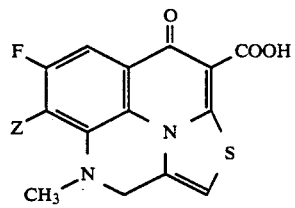

wherein Z is

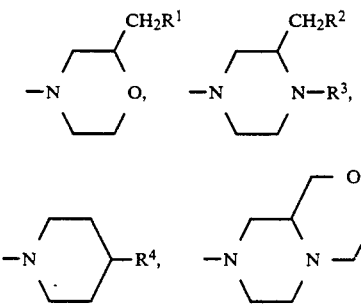

or

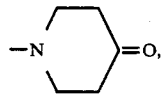

in which $R^1$ is hydrogen atom, a halogen atom, hydroxy or a lower alkyloxy; $R^2$ is a halogen atom, hydroxy or a lower alkyloxy; $R^3$ is a lower alkyl; and $R^4$ is hydroxy or a di(lower alkyl)amino, and a pharmaceutically acceptable salt thereof, which have excellent antibacterial activities and are useful as an antibacterial agent, a pharmaceutical composition containing the same, and process for preparing the same.

8 Claims, No Drawings

QUINOLINECARBOXYLIC ACID DERIVATIVES, ANTIBACTERIAL AGENT CONTAINING THE SAME

The present invention relates to novel quinolinecarboxylic acid derivatives, an antibacterial agent containing said compound as an active ingredient, a process for preparing said compound and a novel intermediate compound used for preparing said compound. More particularly, the present invention relates to novel quinolinecarboxylic acid derivatives represented by the following formula (I):

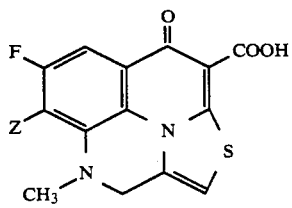

wherein Z is

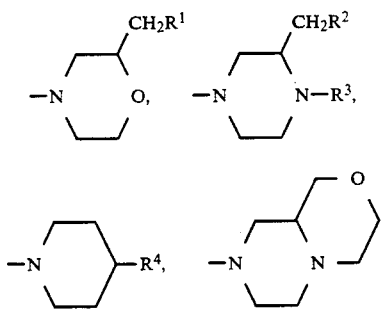

or

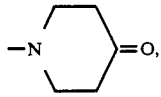

in which $R^1$ is hydrogen atom, a halogen atom, hydroxy or a lower alkyloxy; $R^2$ is a halogen atom, hydroxy or a lower alkyloxy; $R^3$ is a lower alkyl; and $R^4$ is hydroxy or a di(lower alkyl)amino, and a pharmaceutically acceptable salt thereof, an antibacterial agent containing said compound (I) as an active ingredient, a process for preparing said compound (I) and novel intermediate compound used for preparing said compound (I).

PRIOR ART

Since the finding of nalidixic acid as a synthetic antibacterial agent, various quinolinecarboxylic acid derivatives including condensed tricyclic compounds and condensed tetracyclic compounds have hitherto been examined for aiming at the improvement of an antibacterial activity. For example, U.S. Pat. No. 4,382,892 discloses condensed tribyclic compounds having a pyrido[1,2,3-de][1,4]benzoxazine ring including the following compound (X), and further European Patent Publication No. 286089 (corresponding to U.S. Pat. No. 4,808,584, divisional application thereof U.S. Pat. No. 4,853,469) and Proceeding of the 109th Annual Meeting of the Pharmaceutical Society of Japan, Nagoya 1989, Vol. IV, page 30 disclose condensed tetracyclic compounds having a 9,1-epoxymethano-5H-thiazolo[3,2-a]quinoline ring including the following compound (Y).

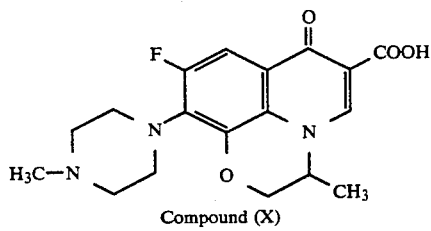

Compound (X)

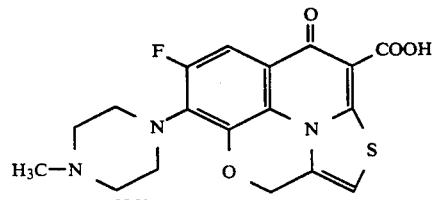

Compound (Y)

However, the above publications do not disclose the condensed tetracyclic compounds (I) of the present invention having a 9,1-iminomethano-5H-thiazolo[3,2-a]quinoline ring.

Some condensed tetracyclic compounds having 9,1-iminomethano-5H-thiazolo[3,2-a]quinoline ring have been disclosed in U.S. Pat. No. 4,971,967 issued on Nov. 20, 1990 which is later than the priority date (Aug. 30, 1990) of this application. The invention of the above U.S. patent has been invented by Kondo et al. who are the same inventors as in the present invention, and further, the U.S. patent does not disclose the novel compounds of the formula (I) of the present invention.

BRIEF SUMMARY OF THE INVENTION

The present inventors have studied to find novel quinolinecarboxylic acid derivatives having condensed teteracyclic ring and having improved antibacterial activities and found that the novel quinolinecarboxylic acid derivatives having condensed tetracyclic ring of the formula (I) as described hereinbefore have improved antibacterial activities and are useful as an antibacterial agent.

An object of the present invention is to provide novel quinolinecarboxylic acid derivatives having condensed tetracyclic ring which show improved antibacterial activities. Another object of the present invention is to provide an excellent antibacterial agent containing said compounds as an active ingredient. Still another object of the present invention is to provide a process for preparing said compounds. A further object of the present invention is to provide novel intermediate compounds used for preparing said compounds.

DETAILED DESCRIPTION OF THE INVENTION

The quinolinecarboxylic acid derivative of the present invention are 9,1-iminomethano-5H-thiazolo[3,2-a]quinoline-4-carboxylic acid derivatives of the formula (I) as described hereinbefore and a pharmaceutically acceptable salt thereof, which show potent antibacterial activities.

Through the present specification and claims, the term "lower alkyl" denotes a straight chain or branched chain alkyl having 1 to 4 carbon atoms, such as methyl, ethyl, n-propyl, isopropyl, n-butyl, sec-butyl, and the like. The di(lower acyloxy)boryl denotes a group consisting of one boron atom and two acyloxy groups having 2 to 5 carbon atoms of the formula: —B(OCOR$^3$)$_2$ wherein R$^3$ is as defined above, for example diacetyloxyboryl, dipropionyloxyboryl, dibutyryloxyboryl, and the like.

Suitable examples of the above cyclic amino group (Z) are 2-methylmorpholino, 2-hydroxymethylmorpholino, 2-fluoromethylmorpholino, 2-chloromethylmorpholino, 2-methoxymethylmorpholino, 2-ethoxymethylmorpholino, 4-methyl-3-fluoromethyl-1-piperazinyl, 4-methyl-3-hydroxymethyl-1-piperazinyl, 4-methyl-3-methoxymethyl-1-piperazinyl, 4-hydroxypiperidino, 4-dimethylaminopiperidino, 1,8-diaza-4-oxabicyclo[4.4.0]deca-8-yl, 4-oxopiperidino, and the like.

Among the cyclic amino group (Z), the groups

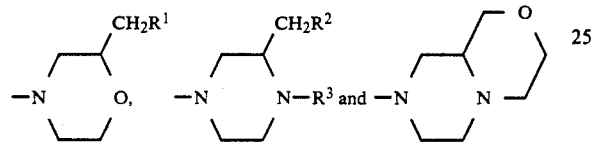

contain an asymmetric carbon and hence, the compounds (I) containing these cyclic amino groups include optical isomers. Thus, the compounds of this invention include also these optical isomers and mixtures thereof.

The compounds of the present invention include a pharmaceutically acceptable salt of the compound of the formula (I). Preferred pharmaceutically acceptable salt of the compound (I) of the present invention are metallic salts such as sodium salt, potassium salt and calcium salt, an ammonium salt and basic amino acid salts such as salts with lysine and arginine at the carboxyl group; and where Z is,

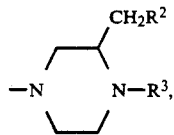

in which R$^2$ and R$^3$ are as defined above, or 4-di(lower alkyl)aminopiperidino, or 1,8-diaza-4-oxabicyclo-[4.4.0]deca-8-yl

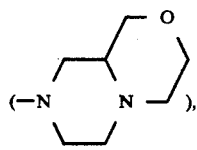

addition salts of inorganic acids such as hydrochloric acid and sulfuric acid, and of organic acids such as maleic acid, fumaric acid, tartaric acid, methanesulfonic acid and p-toluenesulfonic acid are also included.

The compounds of the present invention (I) or a salt thereof can be prepared by, for example, reacting an intermediate compound (II) with a cyclic amine (ZH) or an acid addition salt thereof in a polar organic solvent such as dimethyl sulfoxide or N,N-dimethylformamide in the presence of an acid scavenger, optionally followed by hydrolysis of the product as shown in the following process (A):

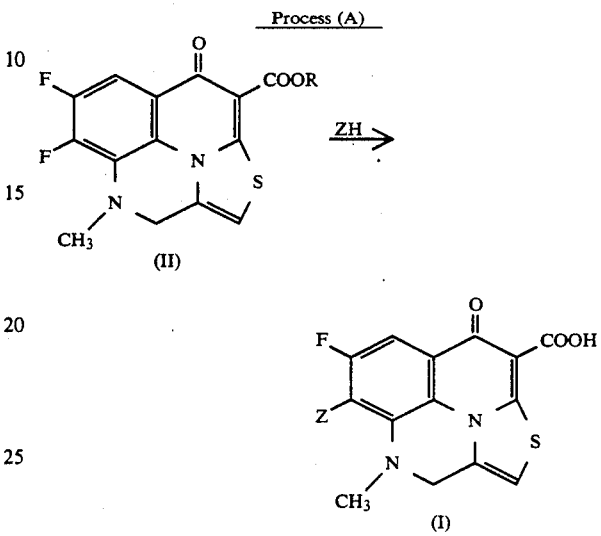

wherein R is hydrogen atom, a lower alkyl, di(lower acyloxy)boryl, or difluoroboryl, and Z is as defined above, That is, the compounds (I) of the present invention can directly be prepared by reacting the compound (II) wherein R is hydrogen atom with a cyclic amine (ZH) or an acid addition salt thereof, or alternatively by reacting the compound (II) wherein R is a lower alkyl, di(lower acyloxy)-boryl [-B(lower acyloxy)$_2$] or difluoroboryl (—BF$_2$) with a cyclic amine (ZH) or an acid addition salt thereof to produce an ester, followed by hydrolysis of said ester.

The acid scavenger includes a tertiary amine such as triethylamine or an inorganic base such as sodium carbonate or potassium carbonate. An excess amount of the above cyclic amine (ZH) can also be employed as the acid scavenger. When the tertiary amine or the inorganic base is employed as the acid scavenger, the reaction is usually carried out in such a way that one mole of the compound (II) is reacted with 1 to 1.5 moles of the cyclic amine (ZH) or the acid addition salt thereof employing 2 to 6 moles of the acid scavenger. When the cyclic amine (ZH) is used as the acid scavenger, one mole of the compound (II) is reacted with an excess amount, usually 3 to 7 moles, of the cyclic amine (ZH).

The reaction temperature in the reaction of the compound (II) and the cyclic amine (ZH) or an acid addition salt thereof may vary in accordance with the kinds of these compounds but is usually in the range of from room temperature to 150° C. When there is used as the compound, (II) a compound in which R is di(lower acyloxy)boryl [referred to as "compound (II-1)"], a compound in which R is difluoroboryl [referred to as "compound (II-2)"], or a compound in which R is hydrogen atom [referred to as "compound (II-3)"], the reaction proceeds rapidly under milder conditions than the reaction using a compound in which R is a lower alkyl [referred to as "compound (II-4)"]. That is, the reaction using the former compound (II-1), (II-2) or (II-3) is usually carried out for about 1 to 30 hours, but on the other hand, the reaction using the latter compound (II-4) is usually carried out for 10 to 250 hours.

The hydrolysis of the reaction product of the compound (II-1) with the cyclic amine (ZH) or an acid addition salt thereof is usually carried out under an acidic condition, preferably hydrochloric acid acidic condition, in a mixture of a water-soluble organic solvent (e.g. acetone, methanol, ethanol, etc.) and water at a temperature of from room temperature to the boiling temperature of the solvent, for 1 to 10 hours.

The hydrolysis of the reaction product of the compound (II-2) or the compound (II-4) with the cyclic amine (ZH) or an acid addition salt thereof is usually carried out under an alkaline condition in a mixture of a water-soluble organic solvent (e.g. acetone, methanol, ethanol, etc.) and water at a temperature of from room temperature to boiling temperature of the solvent, for 1 to 12 hours.

The compounds of the formula (I) wherein Z is 2-hydroxymethylmorpholino [referred to as "compound (I')"] of the present invention can also be prepared by the following process (B).

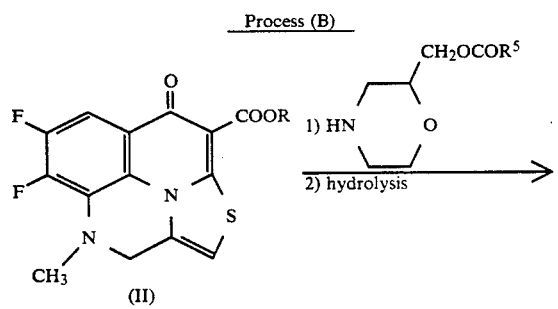

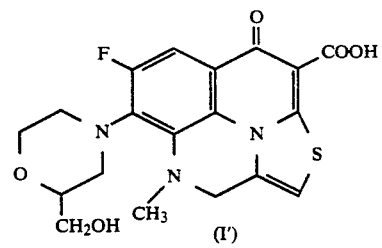

wherein R is as defined above and $R^5$ is a lower alkyl, phenyl or a lower alkyl-substituted phenyl.

That is, the compound (II) is reacted with a 2-acyloxymethylmorpholine or an acid addition salt thereof in the same manner as in the above process (A) and hydrolyzing the reaction product in the conventional manner to give the compound (I') of the present invention.

The compounds (I) of the present invention thus prepared by the above processes, or an acid addition salt thereof, can be isolated and purified by the conventional procedure, for example, silica-gel column chromatography or recrystallization. The compounds (I) of the present invention can also be converted into the pharmaceutically acceptable salts thereof by the conventional procedure.

The intermediate compounds (II) used in the above processes for preparing the compound (I) of the present invention are prepared, for example, by a process as shown in the following reaction scheme:

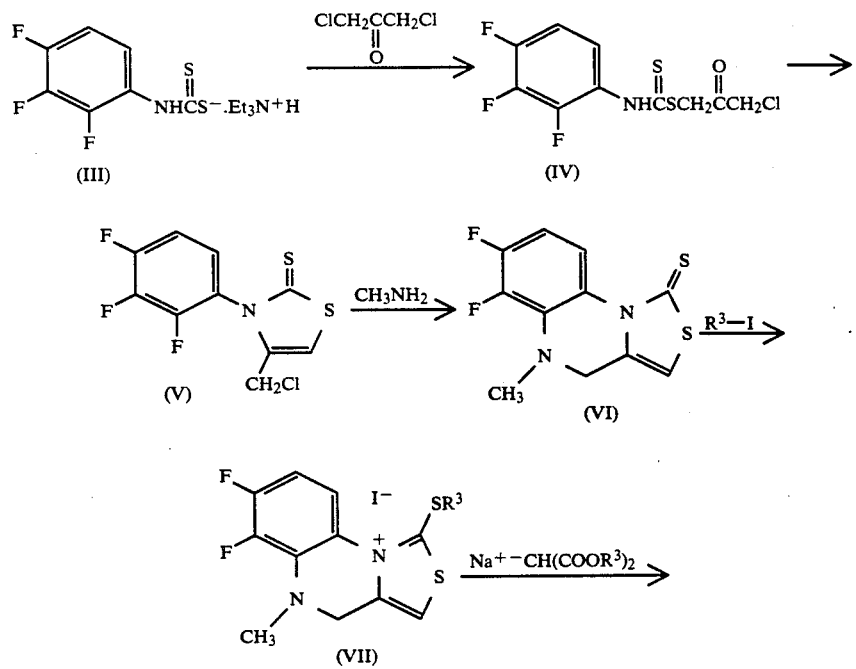

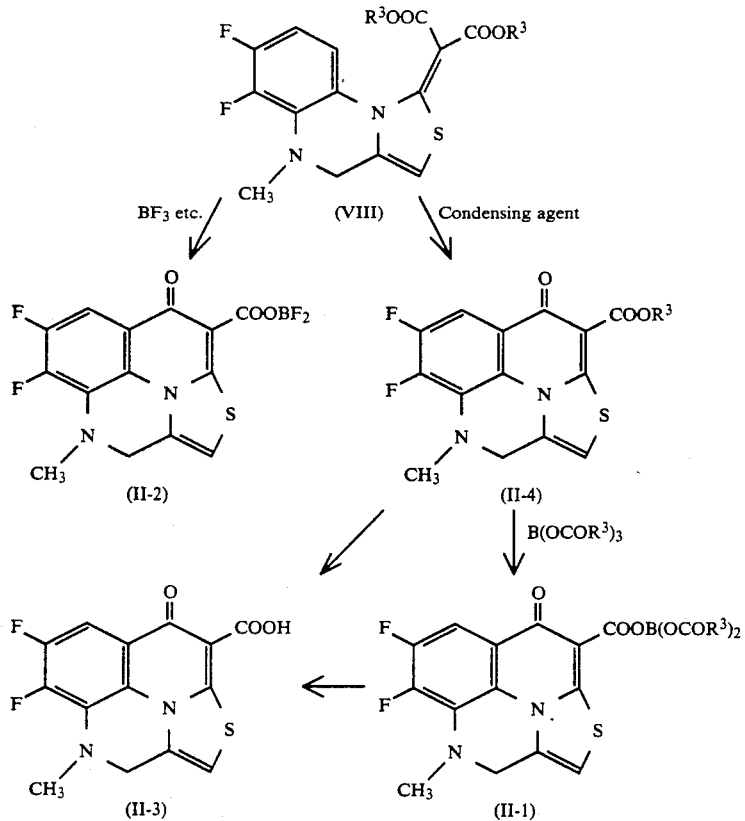

wherein R³ is as defined above.

That is, first the known compound (III) (see European patent publication No. 286089) is reacted with 1,3-dichloroacetone in an organic solvent such as chloroform, ethyl acetate, methylene chloride or a lower alcohol to produce 3-chloro-2-oxopropyl N-(2,3,4-trifluorophenyl)-dithiocarbamate (IV). The compound (IV) is then reacted with an inorganic acid such as hydrogen chloride or sulfuric acid in a lower alcohol such as ethanol or ethyl acetate to give 4-chloromethyl-3-(2,3,4-trifluorophenyl)-2(3H)-1,3-thiazolethione (V). The compound (V) is then reacted with methylamine in an organic solvent such as N,N-dimethylformamide or acetonitrile to give 1H,4H-thiazolo[3,4-a]-quinoxaline-1-thione derivative (VI). The compound (VI) is then reacted with a lower alkyl iodide in a polar solvent such as N,N-dimethylformamide, acetonitrile or ethanol to give a 1-(lower alkyl)thioquinoxalino[1,2-c]thiazolium iodide (VII). Then the compound (VII) is reacted with a di(lower alkyl) malonate sodium, which is prepared from di(lower alkyl) malonate and sodium hydride, in an organic solvent such as tetrahydrofuran or dioxane to give di(lower alkyl) (1H,4H-thiazolo[3,4-a]quinoxalin-1-ylidene)malonate (VIII).

Alternatively, the compound (VIII) can also be prepared by reacting the compound (VI) with phosgene or trichloromethyl chloroformate in an inert solvent such as toluene or benzene and then reacting the obtained product with a di(lower alkyl) malonate in a solvent such as acetonitrile in the presence of a tertiary amine such as triethylamine.

The compound (VIII) is subsequently heated with a condensing agent such as polyphosphoric acid or polyphosphoric acid ethyl ester to cyclize the compound (VIII) to produce the compound (II) wherein R is a lower alkyl, i.e. the compound (II-4).

The compound (II-4) is reacted with a tri(lower acyloxy)borane in a lower alkylcarboxylic acid anhydride to give the compound (II) wherein R is a di(lower acyloxy)-boryl, i.e. the compound (II-1).

The compound (II) wherein R is hydrogen atom, i.e. the compound (II-3) is prepared by hydrolyzing the compound (II-1) under acidic conditions, preferably hydrochloric acid acidic condition, or alternatively by heating the compound (II-4) in conc. sulfuric acid at 60° to 100° C.

The compound (II) wherein R is difluoroboryl, i.e. the compound (II-2), can easily be prepared by reacting the compound (VIII) with boron trifluoride, boron trifluoride complex such as boron trifluoride etherate, hydrofluoroboric acid, or hydrofluoroboric acid salt (e.g. ammonium fluoroborate) in an acid anhydride such as acetic anhydride.

Among the cyclic amines (ZH), the compounds of the formula:

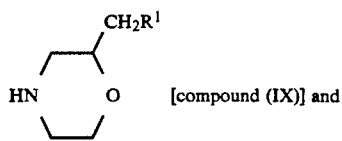

[compound (IX)] and

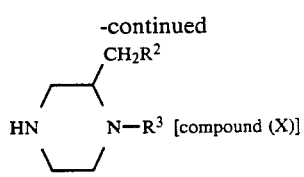

(wherein $R^1$, $R^2$ and $R^3$ are as defined above) and the compound of the formula:

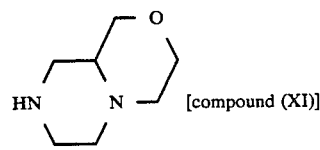

or acid addition salts of them are prepared by the following processes.

That is, the compound (IX) or an acid addition salt thereof can be prepared by hydrogenolysis of the corresponding 4-benzylmorpholine derivative (XII) or an acid addition salt thereof in a lower alcohol or acetic acid or a lower alcohol containing an organic or inorganic acid (e.g. acetic acid, hydrochloric acid, etc.) in the presence of a palladium catalyst as shown in the following reaction scheme:

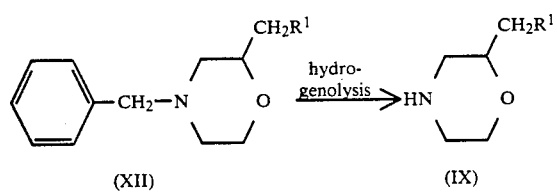

wherein $R^1$ is as defined above.

Among the compounds (XII), the compounds of the formula (XII) wherein $R^1$ is hydrogen atom, a halogen atom or hydroxy [referred to as "compound (XII-1)"] or an acid addition salt thereof can be prepared by reacting an epoxy compound (XIII-1) and N-benzylethanolamine and subjecting to dehydrocondensation reaction in conc. sulfuric acid as shown in the following reaction scheme (cf. Synthetic Communication, Vol. 10, pages 59–73, 1980).

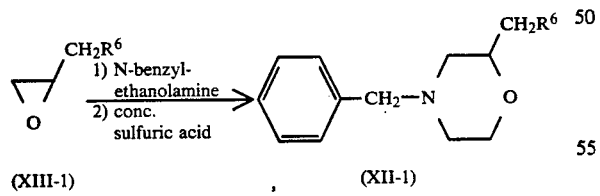

wherein $R^6$ is hydrogen atom, a halogen atom or hydroxy.

The 4-benzyl-2-hydroxymethylmorpholine [the compound (XII 1) wherein $R^6$ is hydroxy] can also be prepared by hydrolysis of 4-benzyl-2-chloromethylmorpholine [the compound (XII-1) wherein $R^6$ is chlorine] (cf. Synthetic Communication, Vol. 10, pages 59–73, 1980).

The 4-benzylmorpholine derivatives (XII) wherein $R^1$ is a lower alkyloxy [referred to as compound (XII-2)] can be prepared by reacting a 4-benzyl-2-halogenomethylmorpholine compound (XII-1) wherein $R^6$ is a halogen atom] or a known 4-benzyl-2-(p-toluenesulfonyloxymethyl)morpholine with a lower alcoholate, or alternatively from an epoxy compound (XIII-2) as shown in the following reaction scheme.

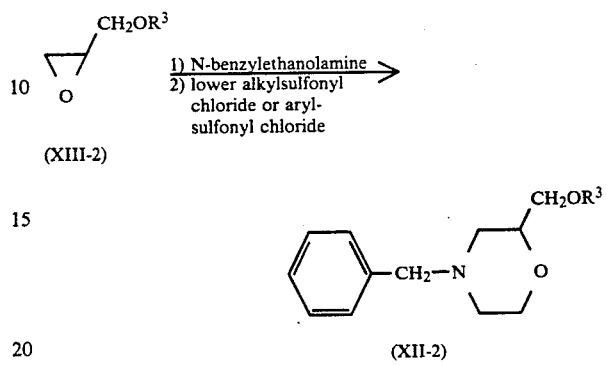

wherein $R^3$ is as defined above.

That is, the epoxy compound (XIII-2) is reacted with N-benzylethanolamine and then reacting the reaction product with a lower alkylsulfonyl chloride (e.g. methanesulfonyl chloride, etc.) or an arylsulfonyl chloride (e.g. p-toluenesulfonyl chloride, etc.) in an aprotic organic solvent in the presence of a phase transfer catalyst (e.g. tris(3,6-dioxaheptyl)amine, 18-crown-6, etc.) and an inorganic base (e.g. potassium hydroxide, sodium hydroxide, etc.) to give the compound (XII-2).

The 2-acyloxymethylmorpholine of the formula:

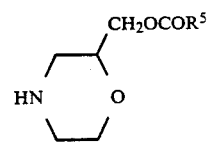

wherein $R^5$ is as defined above, which is used in the above process (B) for preparing the compound (I'), can also be prepared by hydrogenolysis of the corresponding 4-benzyl compound as mentioned hereinabove, said 4-benzyl compound being prepared by acylating 4-benzyl-2-hydroxymethylmorpholine with an acid chloride or an acid anhydride, or alternatively by reacting 4-benzyl-2-(p-toluenesulfonyloxymethyl)morpholine with a carboxylic acid in the presence of an inorganic base (e.g. potassium carbonate, sodium carbonate, etc.) in a polar organic solvent.

Besides, the compound (X) of the formula:

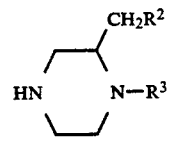

wherein $R^2$ and $R^3$ are as defined above, can also be prepared by hydrogenolysis of the corresponding N-benzyl compound (XIV) in acetic acid or an organic solvent containing an organic or inorganic acid (e.g. acetic acid, hydrochloric acid, etc.) in the presence of a palladium catalyst, followed by treating the resulting acid addition salt of the compound (X) with an alkali as shown in the following reaction scheme:

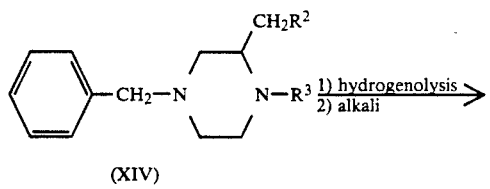

(XIV)

wherein $R^2$ and $R^3$ are as defined above.

The above N benzyl compound (XIV) can be prepared in various manner in accordance with the kinds of the substituents as shown in the following reaction scheme:

methyl can also be prepared by reacting the compound (XV) with formaline and formic acid.

The compound (XVI) obtained above is then treated with a reducing agent (e.g. lithium aluminum hydride, etc.) to give the compound (XIV) wherein $R^2$ is hydroxy [referred to as "compound (XIV-1)"]. The compound (XIV-1) is then reacted with a halogenating agent (e.g. thionyl chloride, thionyl bromide, etc.) in a solvent (e.g. carbon tetra chloride, chloroform, etc.) to give the compound (XIV) wherein $R^2$ is chlorine or bromine atom [referred to as "compound (XIV-2)"]. The compound (XIV-2) is reacted with a lower alcoholate to give the compound (XIV) wherein $R^2$ is a lower alkyloxy [referred to as "compound (XIV-3)"]. The compound (XIV) wherein $R^2$ is fluorine atom or iodine atom [referred to as "compound (XIV-4)"] can be prepared by reacting the compound (XIV-2) with a hydrofluoric acid salt (e.g. sodium fluoride, etc.) or a hydroiodic acid salt (e.g. sodium iodide, etc.).

Moreover, the compound of the formula (XI):

(XI)

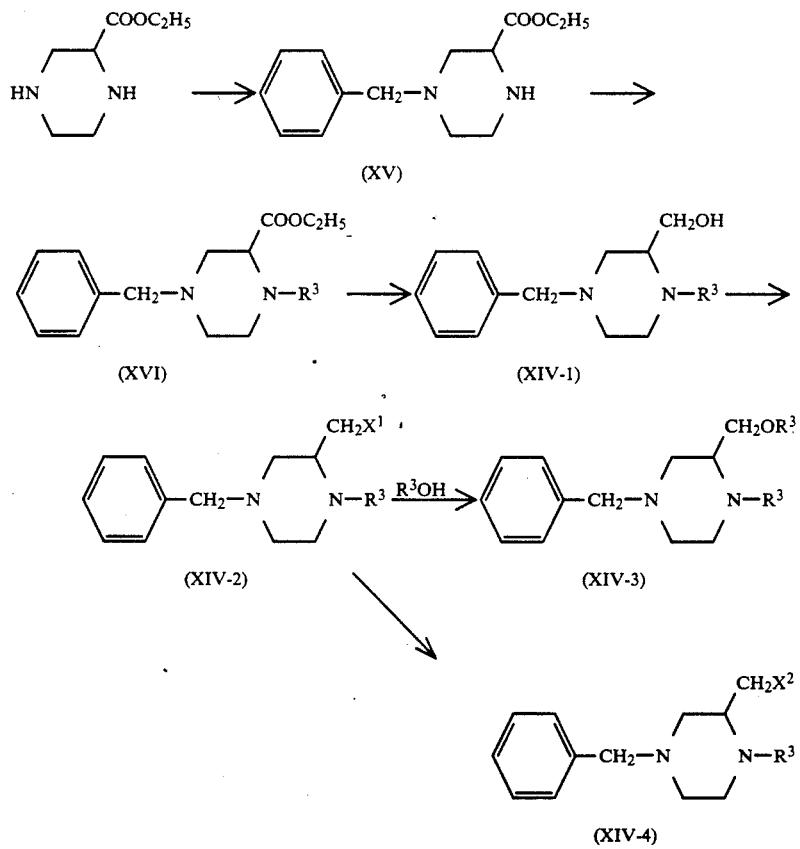

wherein $R^3$ is as defined above, $X^1$ is chlorine atom or bromine atom, and $X^2$ is fluorine atom or iodine atom. That is, ethyl piperazine-2-carboxylate (cf. Helv. Chim. Acta, Vol. 45, page 2383, 1962) or an acid addition salt thereof is reacted with about an equimolar amount of benzyl bromide in an organic solvent (e.g. methylene chloride, ethanol, ethyl acetate, etc.) in the presence of an organic basic compound (e.g. triethylamine, 1,8-diazabicyclo[5.4.0]undec-7-ene, etc.) to give ethyl 4-benzylpiperazine-2-carboxylate (XV). The compound (XV) is reacted with a lower alkyl halide to give the compound (XVI). The compound (XVI) wherein $R^3$ is

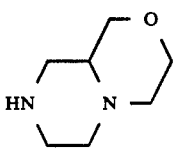

which is one of the cyclic amines (ZH) can be prepared by the process as shown in the following reaction scheme:

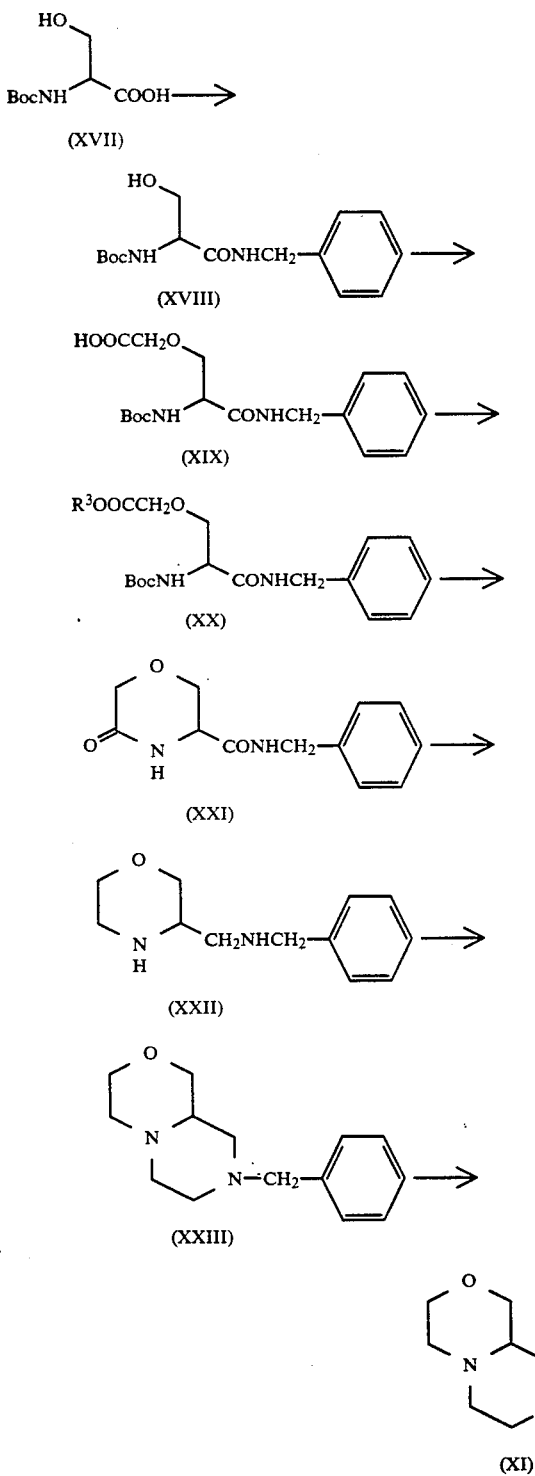

wherein R³ is as defined above, and Boc means tert-butyloxycarbonyl.

That is, N-tert-butloxycarbonylserine (XVII) is condensed with benzylamine in methylene chloride in the presence of a condensing agent such as 1-ethyl-3-(3-dimethylaminopropyl)carbodiimide hydrochloride to give the benzylamide compound (XVIII). The compound (XVIII) is reacted with bromoacetic acid in tetrahydrofuran in the presence of potassium tert-butoxide to give the compound (XIX). The compound (XIX) is then reacted with a lower alkyl halide in the presence of an inorganic basic substance (e.g. potassium carbonate, sodium carbonate, etc.) in a polar organic solvent (e.g. N,N-dimethylformamide, dimethylsulfoxide, etc.) to give the compound (XX) The compound (XX) is treated in 4N hydrogen chloride solution in dioxane to remove the N-tert-butyloxycarbonyl protecting group, followed by cyclizing the resulting compound by treating with a basic substance (e.g. potassium carbonate, sodium carbonate, etc.) in a polar organic solvent (e.g. N,N-dimethylformamide, methanol, etc.) to give the compound (XXI). The compound (XXI) is then treated with a reducing agent (e.g. lithium aluminum hydride, sodium bis(2-methoxyethoxy)aluminum hydride, etc.) in an inert organic solvent (e.g. toluene, ether, etc.) to give the compound (XXII). The compound (XXII) is then reacted with 1,2-dibormoethane in the presence of an inorganic basic substance (e.g. potassium carbonate, sodium carbonate, etc.) in a polar organic solvent (e.g. N,N-dimethylformamide, dimethylsulfoxide, etc.) to give the compound (XXIII). Finally, the compound (XXIII) is subjected to hydrogenolysis in the presence of a palladium catalyst to give the compound (XI). The compound (XI) can easily be converted into its acid addition salt by treating the compound (XI) with an organic or inorganic acid (e.g. acetic acid, hydrochloric acid, etc.).

The compounds (I) of this invention include the optical isomers as mentioned above, and these optical isomers can also be prepared by the processes (A) and (B) by using optically active cyclic amine (ZH) or a derivative thereof.

The optically active cyclic amines can be prepared by resolution of the racemic mixture or alternatively by using an optically active intermediate. The optically active intermediate, for example, optically active 4-benzyl-2-lower alkyloxymethylmorpholine can be prepared by resolution of racemic mixture of known 4-benzyl-2-(p-toluenesulfonyloxymethyl)morpholine (cf. Journal of Medicinal Chemistry, Vol. 19, page 1074, 1976), followed by reacting the resultant with a lower alcoholate. Besides, an optically active 4-benzyl-2-acyloxymethylmorpholine can be prepared by reacting the above-mentioned resolved 4-benzyl-2-(p-toluenesulfonyloxymethyl)morpholine with a carboxylic acid.

The compounds (I) of the present invention and pharmaceutically acceptable salts thereof show excellent antibacterial activities with a low toxicity as shown hereinbelow and are useful as an antibacterial agent.

When the compounds (I) of the present invention and pharmaceutically acceptable salts thereof are used for an antibacterial agent, they are administered to human by oral route or parenterally such as by injection. The dosage form for oral administration includes solid preparations such as tablets, granules, powders, fine granules and hard capsules as well as liquid preparations such as syrups and soft capsules. The pharmaceutical preparations can be prepared by the conventional procedure. Tablets, granuls, powders and fine granules are prepared by mixing the compound (I) of the present invention or a pharmaceutically acceptable salt thereof with conventional pharmaceutically acceptable nontoxic carriers such as lactose, starch, crystalline cellulose, magnesium stearate, hydroxypropyl cellulose, talc, and the like. Hard capsuls are prepared by packing the above fine granules or powders into capsules. Syrups are prepared by dissolving or suspending the compound (I) of the present invention or a pharmaceutically acceptable salt thereof in an aqueous solution containing white sugar, carboxymethyl cellulose and the like. Soft capsules are prepared by dissolving or suspending the compound (I) of the present invention or a pharmaceutically acceptable salt thereof in fatty diluents such as vegetable oils, oil emulsions and glycols and packing the solution or suspension into soft capsules.

Injections are prepared by dissolving or suspending the compound (I) of the present invention or a pharmaceutically acceptable salt thereof in physiological saline or in fatty diluents such as vegetable oils, oil emulsions and glycols and aseptically packing the solution or emulsion in ampoules or vials.

The dose of the compound (I) of the present invention, though it may vary depending on an age or a body weight of patients or severity of diseases, is generally in the range of from 0.5 to 30 mg/kg of body weight/day, preferably from 2 to 20 mg/kg of body weight/day [as the compound (I)], which may be administered once a day or may be divided into 2 to 4 times per day.

The compounds (I) of the present invention and pharmaceutically acceptable salts thereof have a wider antibacterial spectrum and potent antibacterial activities as shown in the following Experiment 1. The compounds (I) of the present invention and pharmaceutically acceptable salts thereof show particularly strong antibacterial activities against Gram positive bacteria and also show strong antibacterial activities against clinically isolated bacteria as demonstrated in the following Experiment 2. Further, tests employing experimental animals prove that the compounds (I) of the present invention and pharmaceutically acceptable salts thereof, e.g. the compounds prepared in Examples 1, 2, 3, 7, 11 and 20, showed excellent protective effects against infection as seen in the following Experiments 3 and 4 and had low toxicity as demonstrated in the following Experiments 5 to 8. Consequently, it is clear that the compounds (I) of the present invention and pharmaceutically acceptable salts thereof are useful as an excellent agent for the prophylaxis and treatment of various infectious diseases, particularly infectious deseases induced by Gram positive bacteria.

The antibacterial activities of the compounds (I) of the present invention and pharmaceutically acceptable salts thereof were tested in the following Experiments. The compounds used in these Experiments include compounds having an asymmetric carbon, but unless the configuration of the asymmeric carbon is specified, these compounds mean racemic compounds.

EXPERIMENT 1

Antibacterial Activities (Minimum Inhibitory Concentration: MIC)

1. Test Compounds

The following compounds of the present invention were tested for antibacterial activities. The known compounds (X) and (Y) as mentioned above were also tested as reference.

Compound (A): 9,1-(Methylimino)methano-7-fluoro-8-(2-methylmorpholino)-5-oxo-5H-thiazolo[3,2-a]quinoline-4-carboxylic acid [compound of Example 1]

Compound (B): 9,1-(Methylimino)methano-7-fluoro-8-(2-hydroxymethylmorpholino)-5-oxo-5H-thiazolo[3,2-a]-quinoline-4-carboxylic acid [compound of Example 2]

Compound (C): 9,1-(Methylimino)methano-7-fluoro-8-(2-fluoromethylmorpholino)-5-oxo-5H-thiazolo[3,2-a]-quinoline-4-carboxylic acid [compound of Example 3]

Compound (D): 9,1-(Methylimino)methano-7-fluoro-8-(2-chloromethylmorpholino)-5-oxo-5H-thiazolo[3,2-a]-quinoline-4-carboxylic acid [compound of Example 4]

Compound (E): 9,1-(Methylimino)methano-7-fluoro-8-(2-methoxymethylmorpholino)-5-oxo-5H-thiazolo[3,2-a] -quinoline-4-carboxylic acid [compound of Example 5]

Compound (F): 9,1-(Methylimino)methano-7-fluoro-8-[(6R)-1,8-diaza-4-oxabicyclo[4.4.0]deca-8-yl]-5-oxo-5H-thiazolo[3,2-a]quinoline-4-carboxylic acid [compound of Example 7]

Compound (G): 9,1-(Methylimino)methano-7-fluoro-8-(4-oxopiperidino)-5-oxo-5H-thiazolo[3,2-a]quinoline-4-carboxylic acid [compound of Example 8]

Compound (H): 9,1-(Methylimino)methano-7-fluoro-8-(4-dimethylaminopiperidino)-5-oxo-5H-thaizolo[3,2-a]-quinoline-4-carboxylic acid [compound of Example 9]

Compound (I): 9,1-(Methylimino)methano-7-fluoro-8-(3-hydroxymethyl-4-methyl-1-piperazinyl)-5-oxo-5H-thiazolo[3,2-a]quinoline-4-carboxylic acid hydrochloride [compound of Example 10]

Compound (J): 9,1-(Methylimino)methano-7-fluoro-8-(3-methoxymethyl-4-methyl-1-piperazinyl)-5-oxo-5H-thiazolo[3,2-a]quinoline-4-carboxylic acid hydrochloride [compound of Example 11]

Compound (K): 9,1-(Methylimino)methano-7-fluoro-8-(3-fluoromethyl-4-methyl-1 piperazinyl) 5-oxo-5H-thiazolo[3,2-a]quinoline-4-carboxylic acid hydrochloride [compound of Example 12]

Compound (L): 9,1-(Methylimino)methano-7-fluoro-8-(4-hydroxypiperidino)-5-oxo-5H-thiazolo[3,2-a]quinoline-4-carboxylic acid [compound of Example 13]

Compound (M): 9,1-(Methylimino)methano-7-fluoro-8 -(2S)-2-hydroxymethylmorpholino]-5-oxo-5H-thiazolo[3,2-a]-quinoline-4-carboxylic acid [compound of Example 17]

Compound (N): 9,1-(Methylimino)methano-7-fluoro-8-(2R)-2-hydroxymethylmorpholino]-5-oxo-5H-thiazolo[3,2-a]-quinoline-4-caboxylic acid [compound of Example 18]

Compound (O): 9,1-(Methylimino)methano-7-fluoro-8-(2S)-2-methoxymethylmorpholino)-5-oxo-5H-thiazolo[3,2-a]-quinoline-4-carboxylic acid [compound of Example 21]

Compound (P): 9,1-(Methylimino)methano-7-fluoro-8-(2R)-2-methoxymethylmorpholino)-5-oxo-5H-thiazolo[3,2-a]-quinoline-4-carboxylic acid [compound of Example 22]

Compound (Q): 9,1-(Methylimino)methano-7-fluoro-8-(2-ethoxymethylmorpholino)-5-oxo-5H-thiazolo[3,2-a]-quinoline-4-carboxylic acid (compound of Example 24)

Compound (X): 9-Fluoro-3-methyl-10-(4-methyl-1-piperazinyl)-7-oxo-2,3-dihydro-7H-pyrido[1,2,3-de][1,4]-benzoxazine-6-carboxylic acid (reference compound disclosed in U.S. Pat. No. 4,382,892)

Compound (Y): 9,1-Epoxymethano-7-fluoro-8-(4-methyl-1-piperazinyl)-5-oxo-5H-thiazolo[3,2-a]quinoline-4-carboxylic acid hydrochloride (reference compound disclosed in European Patent Publication No. 286089)

2. Test Method

The compounds of the present invention (A, C, D, F, and L) and the known compound (X) as reference were each dissolved in 0.1N aqueous sodium hydroxide to prepare a solution of 5000 μg/ml in concentration. The compounds of the present invention (B, E, G, H, M, N, O, P and Q) were each dissolved in dimethylsulfoxide to prepare a solution of 5000 μg/ml in concentration. The compounds of the present invention (I, J and K) and the known compound (Y) were each dissolved in sterilized distilled water to prepare a solution of 5000 μg/ml in concentration. Each solution was diluted with sterilized distilled water to prepare a standard solution with a concentration of each test compound: 1000 μg/ml. The test was carried out by a method as appointed by Japan Society of Chemotherapy [cf. Chemotherapy, 29, 76–79 (1981), TOKYO].

As to *Streptococcus pneumoniae* and *Streptococcus pyogenes*, Brain heart infusion broth (manufactured by DIFCO) was used as the medium for the preculture thereof, and a heart infusion agar medium containing 5% defibrinated horse blood (manufactured by Nissui Seiyaku K.K., Japan) was used as the medium for the measurement of minimum inhibitory concentration (MIC). As to other microorganisms, a sensitivity test broth (manufactured by Nissui Seiyaku K.K.) was used as the medium for the preculture thereof, and a sensitivity test agar medium (manufactured by Nissui Seiyaku K.K.) was used as the medium for the measurement of MIC.

3. Results

The test results are shown in Tables 1-1 to 1-4.

TABLE 1

| Microorganisms | Gram | Min. inhib. concentr. (MIC: μg/ml) Compounds of the present invention | | | | | | | | | |
|---|---|---|---|---|---|---|---|---|---|---|---|
| | | A | B | C | D | E | F | G | H | I | J |
| *Staphylococcus aureus* FDA 209P JC-1 | + | 0.013 | 0.013 | 0.013 | 0.013 | 0.025 | 0.025 | 0.013 | 0.10 | 0.20 | 0.05 |
| *Staphylococcus aureus* IID 803 | + | ≦0.006 | 0.013 | ≦0.006 | ≦0.006 | 0.013 | 0.013 | ≦0.006 | 0.10 | 0.20 | 0.10 |
| *Staphylococcus aureus* Terajima (IID 670) | + | 0.013 | 0.025 | 0.013 | 0.025 | 0.025 | 0.05 | 0.013 | 0.05 | 0.20 | 0.10 |
| *Staphylococcus aureus* MS-353 | + | 0.013 | 0.025 | 0.013 | 0.013 | 0.013 | 0.025 | ≦0.006 | 0.10 | 0.39 | 0.10 |
| *Staphylococcus aureus* Cowan I (IID 975) | + | 0.013 | 0.013 | 0.013 | 0.013 | ≦0.006 | 0.025 | ≦0.006 | 0.05 | 0.20 | 0.05 |
| *Staphylococcus aureus* ATCC 9144 | + | 0.013 | ≦0.006 | 0.013 | 0.013 | 0.013 | 0.025 | ≦0.006 | 0.05 | 0.10 | 0.10 |
| *Staphylococcus aureus* FDA 243 | + | ≦0.006 | ≦0.006 | ≦0.006 | ≦0.006 | ≦0.006 | 0.013 | ≦0.006 | 0.05 | 0.10 | 0.05 |
| *Staphylococcus epidermidis* IAM 1296 | + | 0.05 | 0.05 | 0.025 | 0.025 | 0.05 | 0.05 | 0.013 | 0.20 | 0.20 | 0.20 |
| *Streptococcus pyogenes* Su | + | 0.025 | 0.025 | 0.025 | 0.025 | 0.05 | 0.05 | 0.013 | 0.05 | 0.05 | 0.10 |
| *Streptococcus pyogenes* Cook | + | 0.025 | 0.025 | 0.05 | 0.05 | 0.05 | 0.05 | 0.025 | 0.05 | 0.05 | 0.10 |
| *Streptococcus pyogenes* Sv | + | 0.025 | 0.05 | 0.05 | 0.05 | 0.05 | 0.05 | 0.025 | 0.05 | 0.10 | 0.10 |
| *Streptococcus pneumoniae* IID 552 | + | 0.013 | 0.025 | 0.025 | 0.05 | 0.05 | 0.05 | 0.025 | 0.05 | 0.10 | 0.05 |
| *Streptococcus pneumoniae* IID 554 | + | 0.05 | 0.05 | 0.05 | 0.05 | 0.05 | 0.05 | 0.025 | 0.05 | 0.05 | 0.10 |
| *Bacillus subtilis* ATCC 6633 | + | ≦0.006 | ≦0.006 | ≦0.006 | ≦0.006 | ≦0.006 | 0.013 | ≦0.006 | 0.05 | 0.10 | 0.05 |
| *Bacillus cereus* IAM 1029 | + | 0.013 | 0.025 | 0.013 | 0.025 | 0.025 | 0.025 | 0.013 | 0.05 | 0.20 | 0.10 |
| *Micrococcus luteus* ATCC 9341 | + | 0.10 | 0.10 | 0.10 | 0.05 | 0.10 | 0.20 | 0.05 | 0.39 | 0.39 | 0.39 |
| *Escherichia coli* NIHJ JC-2 | − | 0.10 | 0.10 | 0.20 | 0.20 | 0.20 | 0.39 | 0.10 | 0.20 | 0.20 | 0.39 |
| *Klebsiella pneumoniae* PCI-602 | − | ≦0.006 | ≦0.006 | ≦0.006 | 0.025 | 0.025 | 0.013 | ≦0.006 | 0.025 | 0.025 | 0.05 |
| *Pseudomonas aeruginosa* NCTC 10490 | − | 0.39 | 0.39 | 0.39 | 0.39 | 1.56 | 0.78 | 0.39 | 0.78 | 0.78 | 1.56 |
| *Proteus mirabilis* IFO 3849 | − | 0.20 | 0.39 | 0.20 | 0.39 | 0.78 | 0.78 | 0.20 | 0.78 | 0.78 | 1.56 |
| *Enterobacter cloacae* 963 | − | 0.20 | 0.20 | 0.20 | 0.39 | 0.78 | 0.78 | 0.20 | 0.39 | 0.20 | 0.39 |
| *Acinetobacter calcoaceticus* Ac 54 | − | ≦0.006 | ≦0.006 | ≦0.006 | ≦0.006 | 0.013 | 0.013 | ≦0.006 | 0.10 | 0.10 | 0.10 |

| Microorganisms | Gram | Min. inhib. concentr. (MIC: μg/ml) | | | | | | | | |
|---|---|---|---|---|---|---|---|---|---|---|
| | | Compounds of the present invention | | | | | Compds. of the invention | | Known comp. | |
| | | K | L | M | N | O | P | Q | X | Y |
| *Staphylococcus aureus* FDA 209P JC-1 | + | 0.05 | 0.013 | 0.013 | 0.013 | 0.025 | 0.05 | 0.10 | 0.39 | 0.20 |
| *Staphylococcus aureus* IID 803 | + | 0.05 | ≦0.006 | 0.013 | 0.013 | 0.013 | 0.025 | 0.05 | 0.39 | 0.20 |

TABLE 1-continued

| Organism | +/- | | | | | | | | | |
|---|---|---|---|---|---|---|---|---|---|---|
| Staphylococcus aureus Terajima (IID 670) | + | 0.05 | 0.013 | 0.025 | 0.025 | 0.025 | 0.05 | 0.10 | 0.39 | 0.10 |
| Staphylococcus aureus MS-353 | + | 0.05 | 0.013 | 0.025 | 0.025 | 0.013 | 0.025 | 0.10 | 0.78 | 0.10 |
| Staphylococcus aureus Cowan I (IID 975) | + | 0.05 | ≦0.006 | 0.013 | 0.013 | ≦0.006 | ≦0.006 | 0.05 | 0.39 | 0.10 |
| Staphylococcus aureus ATCC 9144 | + | 0.05 | ≦0.006 | ≦0.006 | ≦0.006 | 0.025 | 0.013 | 0.025 | 0.39 | 0.05 |
| Staphylococcus aureus FDA 243 | + | 0.05 | ≦0.006 | ≦0.006 | ≦0.006 | ≦0.006 | ≦0.006 | 0.05 | 0.39 | 0.05 |
| Staphylococcus epidermidis IAM 1296 | + | 0.10 | 0.013 | 0.05 | 0.05 | 0.05 | 0.05 | 0.10 | 0.78 | 0.39 |
| Streptococcus pyogenes Su | + | 0.05 | 0.025 | 0.025 | 0.025 | 0.05 | 0.05 | 0.20 | 0.78 | 0.10 |
| Streptococcus pyogenes Cook | + | 0.10 | 0.025 | 0.05 | 0.025 | 0.05 | 0.05 | 0.20 | 0.78 | 0.10 |
| Streptococcus pyogenes Sv | + | 0.10 | 0.025 | 0.05 | 0.05 | 0.05 | 0.10 | 0.39 | 0.78 | 0.20 |
| Streptococcus pneumoniae IID 552 | + | 0.05 | 0.013 | 0.05 | 0.025 | 0.05 | 0.05 | 0.39 | 0.78 | 0.10 |
| Streptococcus pneumoniae IID 554 | + | 0.10 | 0.05 | 0.05 | 0.05 | 0.05 | 0.10 | 0.39 | 0.78 | 0.20 |
| Bacillus subtilis ATCC 6633 | + | 0.013 | ≦0.006 | ≦0.006 | ≦0.006 | 0.013 | ≦0.006 | 0.05 | 0.10 | 0.10 |
| Bacillus cereus IAM 1029 | + | 0.05 | 0.013 | 0.025 | 0.025 | 0.025 | 0.025 | 0.10 | 0.39 | 0.39 |
| Micrococcus luteus ATCC 9341 | + | 0.39 | 0.10 | 0.20 | 0.10 | 0.10 | 0.20 | 0.39 | 3.13 | 1.56 |
| Escherichia coli NIHJ JC-2 | − | 0.20 | 0.10 | 0.10 | 0.20 | 0.20 | 0.20 | 0.78 | 0.10 | 0.10 |
| Klebsiella pneumoniae PCI-602 | − | 0.013 | ≦0.006 | ≦0.006 | ≦0.006 | 0.013 | 0.025 | 0.20 | 0.05 | 0.025 |
| Pseudomonas aeruginosa NCTC 10490 | − | 0.78 | 0.39 | 0.39 | 0.39 | 0.78 | 1.56 | 1.56 | 1.56 | 0.78 |
| Proteus mirabilis IFO 3849 | − | 0.39 | 0.20 | 0.39 | 0.39 | 0.78 | 0.78 | 1.56 | 0.39 | 0.20 |
| Enterobacter cloacae 963 | − | 0.20 | 0.20 | 0.20 | 0.39 | 0.78 | 1.56 | 1.56 | 0.20 | 0.10 |
| Acinetobacter calcoaceticus Ac 54 | − | 0.025 | ≦0.006 | ≦0.006 | ≦0.006 | 0.013 | 0.013 | 0.05 | 0.39 | 0.20 |

Experiment 2

In Vitro Antibacterial Activity Against Clinical Isolates

1. Test Compounds

The same as in Experiment 1 [that is, the compounds (A) to (Q) of the present invention and known compounds (X) and (Y)].

2. Method

The compounds (A), (C), (D), (F) and (L) of the present invention and the known compound (X) were dissolved in 0.1N aqueous sodium hydroxide, the compounds (B), (E), (G), (H), (M), (N), (O), (P), and (Q) of the present invention in dimethylsulfoxide, and the compounds (I), (J) and (K) of the present invention and the known compound (Y) in sterilized distilled water, to prepare a solution of 5000 μg/ml in concentration, respectively. The above solutions were then diluted with sterilized distilled water to prepare a standard solution with a concentration of the test compound: 1000 μg/ml each. The test was carried out by a method appointed by Japan Society of Chemotherapy (Chemotherapy, 29, 76-79 (1981), TOKYO) to measure minimum inhibitory concentration (MIC) against 25 strains of clinically isolated Staphylococcus aureus including 16 methicillin resistant strains having MIC more than 6.25 μg/ml against methicillin, 25 strains of clinically isolated Staphylococcus epidermidis, 25 strains of clinically isolated Enterococcus faecalis, and 25 strains of clinically isolated Enterococcus faecium, from which there were calculated a range of MIC ($MIC_{range}$) of the test compound against these resistant strains, a minimum concentration for inhibiting the growth of the strains by 50% ($MIC_{50}$) and a minimum concentration for inhibiting the growth of the strains by 90% ($MIC_{90}$).

For the preculture of each microorganism, there was used as the medium a sensitivity test broth (manufactured by Nissui Seiyaku K.K., Japan), and for the measurement of MIC, there was used a sensitivity test agar medium (manufactured by Nissui Seiyaku K.K.).

The clinically isolates used above were isolated from November 1988 to June 1989 and were obtained from Research Section, Tokyo Clinical Research Center.

3. Results

The test results are shown in Table 2.

TABLE 2

| | Test microorganisms | | | | | |
|---|---|---|---|---|---|---|
| | Staphylococcus aureus | | | Staphylococcus epidermidis | | |
| Test compds. | $MIC_{range}$ (μg/ml) | $MIC_{50}$ (μg/ml) | $MIC_{90}$ (μg/ml) | $MIC_{range}$ (μg/ml) | $MIC_{50}$ (μg/ml) | $MIC_{90}$ (μg/ml) |
| (A) | ≦0.006–0.20 | ≦0.006 | 0.20 | ≦0.006–0.39 | 0.013 | 0.20 |

TABLE 2-continued

| | | | | | | |
|---|---|---|---|---|---|---|
| (B) | ≦0.006–0.78 | 0.013 | 0.78 | ≦0.006–0.78 | 0.025 | 0.39 |
| (C) | ≦0.006–0.20 | 0.013 | 0.20 | ≦0.006–0.39 | 0.013 | 0.39 |
| (D) | ≦0.006–0.20 | 0.013 | 0.20 | ≦0.006–0.39 | 0.013 | 0.20 |
| (E) | ≦0.006–0.78 | 0.013 | 0.78 | ≦0.006–0.39 | 0.05 | 0.39 |
| (F) | 0.013–0.78 | 0.025 | 0.78 | 0.013–1.56 | 0.05 | 0.78 |
| (G) | ≦0.006–0.39 | ≦0.006 | 0.20 | ≦0.006–0.20 | 0.013 | 0.20 |
| (H) | 0.05–3.13 | 0.10 | 3.13 | 0.05–3.13 | 0.05 | 3.13 |
| (I) | 0.10–12.5 | 0.20 | 6.25 | 0.05–3.13 | 0.10 | 3.13 |
| (J) | 0.05–6.25 | 0.10 | 3.13 | 0.05–6.25 | 0.10 | 3.13 |
| (K) | 0.025–1.56 | 0.05 | 1.56 | 0.05–1.56 | 0.05 | 0.78 |
| (L) | ≦0.006–0.39 | ≦0.006 | 0.39 | ≦0.006–0.39 | 0.013 | 0.39 |
| (M) | ≦0.006–0.78 | 0.013 | 0.78 | ≦0.006–0.78 | 0.025 | 0.39 |
| (N) | ≦0.006–0.78 | 0.013 | 0.78 | ≦0.006–0.78 | 0.025 | 0.39 |
| (O) | ≦0.006–0.78 | 0.013 | 0.78 | ≦0.006–0.78 | 0.05 | 0.39 |
| (P) | ≦0.006–0.78 | 0.013 | 0.78 | ≦0.006–0.78 | 0.05 | 0.39 |
| (Q) | ≦0.006–0.78 | 0.013 | 0.78 | ≦0.006–0.78 | 0.025 | 0.39 |
| (X) | 0.39–50 | 1.56 | 25 | 0.20–50 | 0.78 | 25 |
| (Y) | 0.05–12.5 | 0.20 | 12.5 | 0.025–25 | 0.10 | 12.5 |

| | Test microorganisms | | | | | |
|---|---|---|---|---|---|---|
| | Enterococcus faecalis | | | Enterococcus faecium | | |
| Test compds. | $MIC_{range}$ (μg/ml) | $MIC_{50}$ (μg/ml) | $MIC_{90}$ (μg/ml) | $MIC_{range}$ (μg/ml) | $MIC_{50}$ (μg/ml) | $MIC_{90}$ (μg/ml) |
| (A) | 0.025–3.13 | 0.10 | 3.13 | 0.05–6.25 | 0.78 | 3.13 |
| (B) | 0.05–3.13 | 0.20 | 3.13 | 0.10–25 | 1.56 | 6.25 |
| (C) | 0.05–3.13 | 0.10 | 3.13 | 0.05–6.25 | 0.78 | 3.13 |
| (D) | 0.05–3.13 | 0.20 | 1.56 | 0.05–3.13 | 0.39 | 3.13 |
| (E) | 0.10–6.25 | 0.20 | 6.25 | 0.10–12.5 | 3.13 | 6.25 |
| (F) | 0.05–6.25 | 0.20 | 6.25 | 0.20–6.25 | 1.56 | 6.25 |
| (G) | 0.025–1.56 | 0.05 | 1.56 | 0.025–3.13 | 0.39 | 3.13 |
| (H) | 0.20–6.25 | 0.39 | 3.13 | 0.20–25 | 1.56 | 12.5 |
| (I) | 0.20–12.5 | 0.39 | 12.5 | 0.20–25 | 3.13 | 12.5 |
| (J) | 0.20–12.5 | 0.39 | 12.5 | 0.39–25 | 3.13 | 12.5 |
| (K) | 0.20–6.25 | 0.39 | 6.25 | 0.20–12.5 | 1.56 | 12.5 |
| (L) | 0.05–1.56 | 0.05 | 1.56 | 0.05–6.25 | 0.39 | 3.13 |
| (M) | 0.05–3.13 | 0.20 | 3.13 | 0.10–25 | 1.56 | 3.13 |
| (N) | 0.05–3.13 | 0.20 | 3.13 | 0.10–25 | 1.56 | 6.25 |
| (O) | 0.05–3.13 | 0.20 | 3.13 | 0.10–12.5 | 3.13 | 6.25 |
| (P) | 0.10–6.25 | 0.20 | 6.25 | 0.20–12.5 | 3.13 | 12.5 |
| (Q) | 0.05–6.25 | 0.39 | 6.25 | 0.20–25 | 3.13 | 12.5 |
| (X) | 1.56–100 | 3.13 | 50 | 1.56–>100 | 25 | 100 |
| (Y) | 0.20–6.25 | 0.39 | 6.25 | 0.39–12.5 | 3.13 | 6.25 |

EXPERIMENT 3

Effect on Treatment of General Infectious Disease

1. Test Compounds

Compound (A): 9,1-(Methylimino)methano-7-fluoro-8-(2-methylmorpholino)-5-oxo-5H-thiazolo[3,2-a]quinoline-4-carboxylic acid [compound of Example 1]

Compound (B): 9,1-(Methylimino)methano-7-fluoro-8-(2-hydroxymethylmorpholino)-5-oxo-5H-thiazolo[3,2-a]quinoline-4-carboxylic acid [compound of Example 2]

Compound (C): 9,1-(Methylimino)methano-7-fluoro-8-(2-fluoromethylmorpholino)-5-oxo-5H-thiazolo[3,2-a]quinoline-4carboxylic acid [compound of Example 3]

Compound (F): 9,1-(Methylimino)methano-7-fluoro-8-[(6R)-1,8-diaza-4-oxabicyclo[4.4.0]deca-8-yl]-5-oxo-5H-thiazolo-[3,2-a]quinoline-4-carboxylic acid [compound of Example 7]

Compound (J): 9,1-(Methylimino)methano 7-fluoro-8-(3-methoxymethyl-4-methyl-1-piperazinyl)-5-oxo-5H-thiazolo[3,2-a]quinoline-4-carboxylic acid hydrochloride [compound of Example 11]

Compound (X): 9-Fluoro-3-methyl-10-(4-methyl-1-piperazinyl)-7-oxo-2,3-dihydro-7H-pyrido[1,2,3-de][1,4]benzoxazine-6-carboxylic acid (reference compound disclosed in U.S. Pat. No. 4,382,892)

Compound (Y): 9,1-Epoxymethano-7-fluoro-8-(4-methyl-1-piperazinyl)-5-oxo-5H-thiazolo[3,2-a]quinoline-4-carboxylic acid hydrochloride (reference compound disclosed in European Patent Publication No. 286089)

2. Test Microorganism

Staphylococcus aureus IID 803

3. Method

The test microorganism was subjected to standing culture in Brain heart infusion broth (manufactured by DIFCO) at 37° C. for 16 to 18 hours. The culture was then diluted with PBS (Dulbecco's phosphate buffered saline) to adjust the concentration of bacteria to $4 \times 10^7$–$8 \times 10^7$ CFU/ml. The mixture was mixed with an equivalent amount of 10% (w/v) Mucin (BACTO MUCIN BACTERIOLOGICAL, manufactured by Difco Co.) to prepare a bacterial suspension. The thus prepared bacterial suspension (0.5 ml each) was intraperitoneally inoculated to ddY male mice (5 weeks age, weighing 24–27 g, 5 mice in each group), to infect the animals, by which systemic infectious model was prepared.

One hour after the infection, the compound (A), (B), (C) or (F) of the present invention or the known compound (X) suspended in 1% (w/v) aqueous gum arabic or the compound (J) of the present invention or the known compound (Y) dissolved in sterilized distilled water was orally adiministered to mice.

The mice were daily observed for one week, and from the survival number of mice after one week, the 50% effective dose (ED$_{50}$) was calculated by Weil method. This test was repeated several times and the average of ED$_{50}$ was calculated.

4. Results

The test results are shown in Table 3.

TABLE 3

| Test compounds | ED$_{50}$ (mg/kg) |
|---|---|
| Compound (A) | 3.5 |
| Compound (B) | 5.1 |
| Compound (C) | 1.9 |
| Compound (F) | 2.3 |
| Compound (J) | 4.4 |
| Compound (X) | 11.4 |
| Compound (Y) | 10.8 |

EXPERIMENT 4

Effect on Treatment of General Infectious Disease

1. Test Compound

Compound (E): 9,1-(Methylimino)methano-7-fluoro-8-(2-methoxymethylmorpholino)-5-oxo-5H-thiazolo[3,2-a]quinoline-4-carboxylic acid (compound of Example 20)

2. Test Microorganism

*Staphylococcus aureus* IID 803

3. Method

The test microorganism was subjected to standing culture in Brain heart infusion broth (manufactured by DIFCO) at 37° C. for 16 to 18 hours. The culture was then diluted with PBS (Dulbecco's phosphate buffered saline) to adjust the concentration of bacteria to $3 \times 10^7$ CFU/ml. The mixture was mixed with an equivalent amount of 10% (w/v) Mucin (BACTO MUCIN BACTERIOLOGICAL, manufactured by Difco Co.) to prepare a bacterial suspension. The thus prepared bacterial suspension (0.5 ml each) was intraperitoneally inoculated to ddY male mice (5 weeks age, weighing 22-29 g, 10 mice in each group), to infect the animals, by which systemic infectious model was prepared. One hour after the infection, a suspension of the test compound in 1% (w/v) aqueous gum arabic was orally adiministered to mice.

The mice were daily observed for one week, and from the survival number of mice after one week, the 50% effective dose (ED$_{50}$) was calculated by Weil method.

4. Results

The test results are shown in Table 4.

TABLE 4

| test compound | ED$_{50}$ (mg/kg) |
|---|---|
| Compound (E) | 1.7 |

EXPERIMENT 5

Acute Toxicity

1. Test Compounds

Compound (A): 9,1-(Methylimino)methano-7-fluoro-8-(2-methylmorpholino)-5-oxo 5H-thiazolo[3,2-a]quinoline-4-carboxylic acid [compound of Example 1]

Compound (B): 9,1-(Methylimino)methano-7-fluoro-8-(2-hydroxymethylmorpholino)-5-oxo-5H-thiazolo[3,2-a]-quinoline-4-carboxylic acid [compound of Example 2]

Compound (C): 9,1-(Methylimino)methano-7-fluoro-8-(2-fluoromethylmorpholino)-5-oxo-5H-thiazolo[3,2-a]-quinoline-4-carboxylic acid [compound of Example 3]

2. Method

The compound (A) or (B) of the present invention was suspended in distilled water to prepare a suspension in concentration of 200 mg/ml and the compound (C) was suspended in distilled water to prepare a suspension in concentration of 100 mg/ml. The suspension was orally administered to ddY male mice (5 weeks age, weighing 19 to 24 g, 5 mice in each group), which had been fasted for 18 hours, at a rate of 2000 mg/kg body weight of the test compound. These mice were observed for the number dead for a week.

3. Results

After administration of the compound (A), (B) or (C) of the present invention at a rate of 2000 mg/kg body weight, no death of mice was observed.

EXPERIMENT 6

Acute Toxicity

1. Method 9,1-(Methylimino)methano-7-fluoro-8-(2-methoxymethylmorpholino)-5-oxo-5H-thiazolo[3,2-a]quinoline-4-carboxylic acid (compound of Example 20) [the compound (E) of the present invention] was suspended in 1% aqueous gum arabic to prepare a suspension in concentration of 100 mg/ml. The suspension was orally administered to F344/DuCrj male and female rats (5 weeks age, weighing 110 to 115 g in male, 91 to 95 g in female, 3 rats in each group), which had been fasted for 5 hours, at a rate of 1000 and 2000 mg/kg body weight of the test compound (E). These rats were observed for the number dead for a week.

2. Results

After administration of the compound (E) of the present invention at a rate of 1000 and 2000 mg/kg body weight, no death of rats was observed.

EXPERIMENT 7

Micronucleus Test

1. Method 9,1-(Methylimino)methano-7-fluoro-8-(2-fluoromethylmorpholino)-5-oxo-5H-thiazolo[3,2-a]quinoline-4-carboxylic acid (compound of Example 3) [the compound (C) of the present invention] was suspended in sterilized distilled water. The suspension was orally administered to ICR male mice (8 weeks age, weighing 30 to 36 g, 3 mice in each group) at a rate of 3000, 1000, 300 or 100 mg/kg body weight of the test compound (C). After 24 hours, these mice were killed and the bone marrow was collected and observed for the presence of micronuclei.

2. Results

The compound (C) of the present invention exhibited no nucleus inducing activity.

EXPERIMENT 8

Micronucleus Test

1. Test Compounds

Compound (B): 9,1-(Methylimino)methano-7-fluoro-8-(2-hydroxymethylmorpholino)-5-oxo-5H-thiazolo[3,2-a]-quinoline-4-carboxylic acid [compound of Example 15]

Compound (E): 9,1-(Methylimino)methano-7-fluoro-8-(2-methoxymethylmorpholino)-5-oxo-5H-thiazolo[3,2-a]-quinoline-4-carboxylic acid (compound of Example 20)

2. Method

The compound (B) or (E) of the present invention was suspended in 1% aqueous gum arabic The suspension was orally administered to ICR male mice (7-8 weeks age, weighing 30 to 39 g, 5 mice in each group) at a rate of 3000, 1000 or 300 mg/kg body weight of the test compound (B) or (E). After 24 hours or 48 hours, these mice were killed and the bone marrow was collected and observed for the presence of micronuclei.

2. Results

The compounds (B) and (E) of the present invention exhibited no nucleus inducing activity.

EXAMPLES

The preparation of the compounds of the present invention is illustrated by means of the following Reference Examples and Examples, but should not be construed to be limited thereto. In these examples, the compounds are racemic mixture unless the configuration of asymmetric carbon is specified.

REFERENCE EXAMPLE 1

Preparation of 3-chloro-2-oxopropyl N-(2,3,4-trifluorophenyl)dithiocarbamate [compound (IV)]

1,3-Dichloroacetone (2.0 g) is added to methylene chloride (100 ml), and thereto is added triethylammonium N-(2,3,4-trifluorophenyl)dithiocarbamate (cf. European Patent Publication 286089) (5.0 g) with stirring at 2° to 5° C. The mixture is stirred for additional 60 minutes and then washed with 3N hydrochloric acid and water in this order. The organic layer is dried over anhydrous sodium sulfate and distilled under reduced pressure to remove the solvent. The residue is crystallized from a mixture of hexane-ethyl acetate-ether to give the title compound (4.2 g).

Mass spectrum (m/e): 313 (M+).

REFERENCE EXAMPLE 2

Preparation of 4-chloromethyl-3-(2,3,4-trifluorophenyl)-2(3H)-thiazolethione [compound (V)]

3-Chloro-2-oxopropyl N-(2,3,4-trifluorophenyl)-dithiocarbamate (4.0 g) is added to 30% hydrogen chloridemethanol solution (15 ml), and the mixture is refluxed for 3 hours. The solvent is distilled off under reduced pressure, and cold water is added to the residue and the mixture is extracted with chloroform. The extract is washed with saline solution, dried over anhydrous sodium sulfate and distilled under reduced pressure to remove the solvent. The residue is recrystallized from cyclohexane to give the title compound (2.6 9) as pale yellow crystals.

M.p. 127°–130° C.

NMR (CDCl$_3$) δ: 4.1 (1H, d, J=13Hz), 4.2 (1H, d, J=13Hz), 6.8 (1H, s), 7.2 (2H, m).

IR (KBr) ν$_{max}$ cm$^{-1}$: 3072, 1516, 1504, 1314, 1260, 1102.

Elementary analysis for C$_{10}$H$_5$NS$_2$F$_3$Cl:

Calcd. (%): C,40.61; H,1.70; N,4.74

Found (%): C,40.59; H,1.80; N,4.71.

REFERENCE EXAMPLE 3

Preparation of 5-methyl-6,7-difluoro-1H,4H-thiazolo[3,4-a]quinoxaline-1-thione [compound (VI)]

4-Chloromethyl-3-(2,3,4-trifluorophenyl)-2(3H)-thiazolethione (2.5 g) is dissolved in acetonitrile (25 ml) and thereto is added 40% solution of methylamine in methanol (3.3 g), and the mixture is stirred at 50° C. for 16 hours. The reaction mixture is evaporated to dryness under reduced pressure, and water is added to the residue and the mixture is extracted with chloroform. The extract is washed with saline solution, dried over anhydrous sodium sulfate and distilled under reduced pressure to remove the solvent. The residue is recrystallized from cyclohexane-ethyl acetate to give the title compound (2.0 g) as yellow crystals.

M.p. 165°–167° C.

NMR (CDCl$_3$) δ: 3.0 (3H, d, J=2.5Hz), 4.0 (2H, d, J=1Hz), 6.4 (1H, t, J=1Hz), 6.9 (1H, dt, J=8Hz, J=9Hz), 9.3 (1H, ddd, J=2.5Hz, J=5Hz, J=9.5Hz).

IR (KBr) ν$_{max}$ cm$^{-1}$: 1502, 1492, 1306, 1290, 1032.

Elementary analysis for C11H$_8$N$_2$S$_2$F$_2$:

Calcd. (%): C,48.87; H,2.98; N,10.36

Found (%): C,49.04; H,2.96; N,10.41.

REFERENCE EXAMPLE 4

Preparation of 5 methyl-6,7-difluoro-1-methylthio-4H-quinoxalino[1,2-c]thiazolium iodide [compound (VII) wherein R$^3$ is methyl]

5-Methyl-6,7-difluoro-1H,4H-thiazolo[3,4-a]quinoxaline-1-thione (0.4 g) and methyl iodide (0.4 g) are dissolved in N,N-dimethylformamide (3 ml), and the mixture is allowed to stand in dark room at room temperature for 40 hours. The precipitates are collected by filtration and washed with acetonitrile and ether in this order to give the title compound (0.5 g) as yellow crystals.

NMR (DMSO-d$_6$) δ: 3.0 (3H, d, J=4Hz), 3.1 (3H, s), 4.4 (2H, s), 7.3 (1H, dt, J=8Hz, J=9.5Hz), 7.9 (1H, ddd, J=2Hz, J=5Hz, J=9.5Hz), 8.0 (1H, s).

REFERENCE EXAMPLE 5

Preparation of diethyl (5-methyl-6,7-difluoro-1H,4H-thiazolo[3,4-a]quinoxalin-1-ylidene)malonate [compound (VIII) in which R$^3$ is ethyl]

Sodium hydride in oil (content, about 60 w/w %) (54 mg) is suspended in tetrahydrofuran (3 ml) and thereto is added dropwise diethyl malonate (0.2 g) at 20° C., and the mixture is stirred for 20 minutes. To the mixture is added 5-methyl-6,7-difluoro-1-methylthio-4H-quinoxalino[1,2-c]-thiazolium iodide (0.5 g) at 10° C., and the mixture is stirred at room temperature for 30 minutes. The reaction mixture is evaporated to dryness under reduced pressure. To the residue is then added water and the undissolved substance is separated by filtration, washed with water, dried, and recrystallized from hexane ethyl acetate to give the title compound (0.34 g) as yellow crystals.

M.p. 146°-148° C.

NMR (CDCl$_3$) δ: 1.2 (6H, t, J=7Hz), 3.1 (3H, d, J=4.5Hz), 3.9 (4H, q, J=7Hz), 4.0 (2H, s), 6.5 (1H, t, J=1Hz), 6.8 (1H, dt, J=8Hz, J=9Hz), 7.3 (1H, ddd, J=2Hz, J=5Hz, J=9Hz).

IR (KBr) $v_{max}$ cm$^{-1}$: 1700, 1642, 1506, 1426, 1294, 1188, 1082.

Elementary analysis for C$_{18}$H$_{18}$N$_2$O$_4$SF$_2$:
Calcd. (%): C,54.54; H,4.58; N,7.07
Found (%): C,54.45; H,4.61; N,6.89.

REFERENCE EXAMPLE 6

Preparation of diethyl (5-methyl-6,7-difluoro-1H,4H-thiazolo[3,4-a]quinoxalin-1-ylidene)malonate [compound (VIII) in which R$^3$ is ethyl]

To 5-methyl-6,7-difluoro-1H,4H-thiazolo[3,4-a]-quinoxaline-1 thione (cf. Reference Example 3) (18 g) are added toluene (110 ml) and trichloromethyl chloroformate (9.74 ml), and the mixture is stirred at 80° C. for 17 hours. The resulting precipitate is separated by decantation, and to the precipitate containing small amount of toluene are added acetonitrile (60 ml) and diethyl malonate (12.88 g). To the mixture is added triethylamine (14.9 g) under ice cooling, and the mixture is stirred at room temperature for 40 minutes. The reaction mixture is evaporated to dryness under reduced pressure. To the residue is then added water and the mixture is extracted with chloroform. The extract is dried over anhydrous sodium sulfate and distilled under reduced pressure to remove the solvent. The residue is washed with isopropyl ether to give the title compound (24.3 g). This product is identical with the diethyl (5-methyl-6,7-difluoro-1H,4H-thiazolo[3,4-a]quinoxalin-1-ylidene)-malonate obtained in Reference Example 5 in the physical properties.

REFERENCE EXAMPLE 7

Preparation of ethyl 9,1-(methylimino)methano-7,8-difluoro-5-oxo-5H-thiazolo[3,2-a]quinoline-4-carboxylate [compound (II-4) in which R$^3$ is ethyl]

A mixture of diethyl (5-methyl-6,7-difluoro-1H,4H-thiazolo[3,4-a]quinoxalin-1-ylidene]malonate (cf. Reference Example 5) (1.2 g) and polyphosphoric acid (10 g) is stirred at 100° C. for 5 hours. To the reaction mixture is added cold water, and the mixture is extracted with chloroform. The extract was washed with a saline solution, dried over anhydrous magnesium sulfate and the solvent is distilled off under reduced pressure. The residue is recrystallized from chloroform-ethanol to give the title compound (0.6 g) as pale yellow crystals.

M.p. decomposed at around 285° C.

NMR (DMSO-d$_6$) δ: 1.3 (3H, t, J=7Hz), 3.2 (3H, d, J=5.5Hz), 4.3 (2H, q, J=7Hz), 4.5 (2H, d, J=1Hz), 7.3 (1H, s), 7.4 (1H, dd, J=7.5Hz, J=10.5Hz).

IR (KBr) $v_{max}$ cm$^{-1}$: 3060, 1708, 1574, 1496, 1478, 1456, 1050.

Elementary analysis for C$_{16}$H$_{12}$N$_2$O$_3$SF$_2$:
Calcd. (%): C,54.85; H,3.45; N,8.00
Found (%): C,54.65; H,3.59; N,7.97.

REFERENCE EXAMPLE 8

Preparation of 9,1-(methylimino)methano-7,8-difluoro-5-oxo-5H-thiazolo[3,2-a]quinoline-4-carboxylic acid [compound (II 3)]

To ethyl 9,1-(methylimino)methano-7,8-difluoro-5-oxo-5H-thiazolo[3,2-a]quinoline-4 carboxylate (1.6 g) is added conc. sulfuric acid (18 ml), and the mixture is stirred at 85° C. for 6 hours. To the reaction mixture is added ice, and the resulting precipitate is separated by filtration and washed with water to give a product (1.25 g) as pale yellow powder. This product is recrystallized from dimethylsulfoxide-ethanol to give the title compound (1.0 g).

M.p. decomposed at around 262° C.

NMR (DMSO-d$_6$) δ: 3.2 (3H, d, J=6Hz), 4.6 (2H, s), 7.5 (1H, s), 7.6 (1H, dd, J=7Hz, J=9Hz), 15.6 (1H, bs).

IR (KBr) $v_{max}$ cm$^{-1}$: 1690, 1552, 1506, 1480, 1472, 1456, 1404.

Elementary analysis for C$_{14}$H$_8$N$_2$O$_3$SF$_2$:
Calcd. (%): C,52.17; H,2.50; N,8.69
Found (%): C,52.07; H,2.77; N,8.47.

REFERENCE EXAMPLE 9

Preparation of 9,1-(methylimino)methano-7,8-difluoro-5-oxo-5H-thiazolo[3,2-a]quinoline-4-carboxylic acid [compound (II-3)]

Dipropionyloxy [9,1-(methylimino)methano-7,8-difluoro-5-oxo-5H-thiazolo[3,2-a]quinoline-4-carboxy]-borane (cf. Example 26 hereinafter) (0.5 g) is suspended in acetone (2 ml) and thereto is added conc. hydrochloric acid (0.15 ml), and the mixture is stirred at room temperature. The resulting solid product is collected by filtration, washed with water, acetone and isopropyl ether in this order, and then recrystallized from dimethylsulfoxide-ethanol to give the title compound (0.36 g).

This product is identical with 9,1-(methylimino)-methano-7,8-difluoro-5-oxo-5H-thiazolo[3,2-a]quinoline-4-carboxylic acid obtained in Reference Example 8 in the physical properties.

REFERENCE EXAMPLE 10

Preparation of 2-methoxymethylmorpholine [compound (IX) in which R$^1$ is methoxy]

2-Methoxymethylmorpholine is prepared by the following two steps.

(1) 4-Benzyl-2-methoxymethylmorpholine

N-Benzylethanolamine (459 g) is mixed with 1,2-epoxy-3-methoxypropane (422 g) and the mixture is stirred at 50° C. for 16 hours and thereafter the excess 1,2-epoxy-3-methoxypropane is distilled off under reduced pressure. The residue is dissolved in 1,4-dioxane (3 liters) and thereto are added powdery potassium hydroxide (692.5 g) and tris(3,6-dioxaheptyl)amine (11.4 g). To the mixture is added dropwise with stirring a solution of p-toluenesulfonyl chloride (809.4 g) in 1,4-dioxane (2 liters) over a period of 1.5 hour, during which the temperature of the reaction mixture raises and the solvent is refluxed. After the dropwise addition, the mixture is stirred for 2 hours, and the undissolved materials are filtered off and washed with ethyl acetate. The filtrate and the washing liquid are combined and distilled under reduced pressure to remove the solvent.

To the residue are added water (600 ml) and conc. hydrochloric acid (300 ml) to make acidic. The aqueous layer is washed with ethyl acetate, made strongly basic by adding sodium hydroxide (160 g) under ice cooling and extracted with ethyl acetate. The ethyl acetate layer is washed with saturated saline solution, dried over anhydrous magnesium sulfate and distilled under reduced pressure to remove the solvent. The obtained residue is distilled under reduced pressure to give the title compound (391.3 g) as colorless liquid.

B.p. 103° C./0.25 mmHg.

Elementary analysis for $C_{13}H_{19}NO_2$:

Calcd. (%): C,70.56; H,8.65; N,6.33

Found (%): C,70.53; H,8.70; N,6.19.

(2) 2-Methoxymethylmorpholine [compound (IX) in which $R^1$ is methoxy]

N-Benzyl-2-methoxymethylmorpholine (412.3 g) is dissolved in methanol (2 liters), and thereto is added 10% palladium-carbon (33 g), and the mixture is stirred under hydrogen pressure of 9 kg/cm$^2$ at 100° C. After completion of the reaction, palladium-carbon is filtered off, and the solvent is distilled off under atmospheric pressure to give a pale yellow oily substance. The oily substance is distilled under reduced pressure to give the title compound (212.3 g) as colorless liquid.

B.p. 90° C./19 mmHg.

NMR (CDCl$_3$) δ: 2.0 (1H, bs), 2.6 (1H, dd, J=12Hz, J=10.5Hz), 2.8-3.0 (3H, m), 3.4 (3H, s), 3.3-3.5 (2H, m), 3.6-3.7 (2H, m), 3.9-4.0 (1H, m).

REFERENCE EXAMPLE 11

Preparation of (2S)-2-methoxymethylmorpholine hydrochloride [compound (IX) in which $R^1$ is methoxy, and 2-position is S-configuration, hydrochloride thereof]

(2S)-2-Methoxymethylmorpholine hydrochloride is prepared by the following three steps.

(1) 4-Benzyl-2-(p-toluenesulfonyloxymethyl)-morpholine:

4-Benzyl-2-hydroxymethylmorpholine (prepared in the same manner as described in Synthetic Communication, Vol. 10, pages 59-73, 1980) (51 g) is dissolved in pyridine (100 ml) and thereto is added p-toluenesulfonyl chloride (51.7 g) under ice cooling, and the mixture is stirred at room temperature for 12 hours. The precipitated crystals are separated by filtration and washed with ethyl acetate to give hydrochloride of the title compound (70 g). The product (50 g) is suspended in water (200 ml) and the mixture is adjusted to pH 10 with 2N aqueous sodium hydroxide, and extracted with ether. The extract is washed with water, dried over anhydrous sodium sulfate and concentrated under reduced pressure to give the title compound (43 g).

NMR (CDCl$_3$) δ: 1.7-2.9 (4H, m), 2.4 (3H, s), 3.4-4.1 (5H, m), 3.5 (2H, s), 7.2-7.5 (7H, m), 7.8 (2H, d, J=9Hz).

(2) (2S)-4-Benzyl-2-methoxymethylmorpholine

In the same manner as described in Journal of Medicinal Chemistry, Vol. 19, pages 1074-1076, 1976, the above 4-benzyl-2-(p-toluenesulfonyloxymethyl)morpholine is glutamic acid (prepared as disclosed in Journal of the Chemical Society, page 706, 1940) to give (2S)-4-benzyl-2-(p-toluenesulfonyloxymethyl)morpholine.N-(p-toluenesulfonyl)-L-glutamic acid salt.

This compound (10 g) is dissolved in methanol (10 ml) and thereto is added 28% sodium methoxide/methanol (53 g), and the mixture is refluxed for 18 hours. The reaction mixture is adjusted to pH 8 with diluted hydrochloric acid and extracted with ether. The extract is washed with water, dried over anhydrous sodium sulfate, and distilled under reduced pressure to remove the solvent. The residue is purified by silica gel column chromatography (eluent, chloroform), and then distilled under reduced pressure to give the title compound (3.5 g) as colorless liquid.

B.p. 119° C./0.25 mmHg.

NMR (CDCl$_3$) δ: 2.0 (1H, dd, J=11Hz, J=10.5Hz), 2.2 (1H, td, J=11Hz, J=3Hz), 2.6 2.7 (1H, m), 2.7 (1H, dt, J=11Hz, J=2Hz), 3.3-4.0 (7H, m), 3.4 (3H, s), 7.2-7.4 (5H, m).

Elementary analysis for $C_{13}H_{19}NO_2$:

Calcd. (%): C,70.56; H,8.65; N,6.33

Found (%): C,70.33; H,8.84; N,6.29.

$[\alpha]_D^{21}$ +28.1° (c=1.0, CH$_3$OH).

(3) (2S)-2-methoxymethylmorpholine hydrochloride (2S)-4-Benzyl-2-methoxymethylmorpholine (3 g) is dissolved in ethanol (50 ml) and thereto are added 4N hydrogen chloride/dioxane (3.4 ml) and 10% palladium-carbon (0.3 g), and the mixture is stirred under hydrogen pressure of 5 kg/cm$^2$ at 40° C. for 6 hours. After removing palladium-carbon, the solvent is distilled off under reduced pressure. The residue is recrystallized from ethyl acetate-methanol to give the title compound (1.8 g).

M.p. 141°-142° C.

NMR (CDCl$_3$) δ: 3.0-3.2 (2H, m), 3.4 (3H, s), 3.3-3.6 (4H, m), 4.0 4.2 (3H, m), 10.0 (2H, br).

Elementary analysis for $C_6H_{13}NO_2$.HCl:

Calcd. (%): C,42.99; H,8.42; N,8.36

Found (%): C,43.10; H,8.40; N,8.28.

$[\alpha]_D^{20}$ −1.7° (c=1.0, CH$_3$OH).

REFERENCE EXAMPLE 12

Preparation of (2R)-2-methoxymethylmorpholine hydrochloride [compound (IX) in which $R^1$ is methoxy, and 2-position is R-configuration, hydrochloride thereof]

(2R)-2-Methoxymethylmorpholine hydrochloride is prepared by the following two steps.

(1) (2R)-4-Benzyl-2-methoxymethylmorpholine:

From the mother liquor in the resolution in Reference Example 11-(2), a fraction rich in (2R)-4-benzyl -2-(p-toluenesulfonyloxymethyl)morpholine is recovered, and in the same manner as described in Journal of Medicinal Chemistry, Vol. 19, pages 1074-1076, 1976, the above product is subjected to resolution with N-(p-toluenesulfonyl)-D-glutamic acid (prepared by the method as disclosed in Journal of the Chemical Society, page 706, 1940) to give (2R)-4-benzyl-2-(p-toluenesulfonyloxymethyl)morpholine.N-(p-toluenesulfonyl)-D-glutamic acid salt.

This compound is reacted with sodium methoxide in the same manner as described in Reference Example 11-(2) to give the title compound.

B.p. 120° C./0.45 mmHg.

NMR (CDCl$_3$) δ: 2.0 (1H, dd, J=11Hz, J=10.5Hz), 2.2 (1H, td, J=11Hz, J=3Hz), 2.6-2.7 (1H, m), 2.7 (1H, dt, J=11Hz, J=2Hz), 3.3-4.0 (7H, m), 3.4 (3H, s), 7.2-7.4 (5H, m).

Elementary analysis for $C_{13}H_{19}NO_2$:

Calcd. (%): C,70.56; H,8.65; N,6.33

Found (%): C,70.38; H,8.84; N,6.26.

$[\alpha]_D^{21}$ −27.9° (c=1.0, CH$_3$OH).

(3) (2R)-2-methoxymethylmorpholine hydrochloride

In the same manner as described in Reference Example 11-(3) except that (2R)-4-benzyl-2-methoxymethylmorpholine is used instead of (2S)-4-benzyl-2-methoxymethylmorpholine, there is obtained the title compound.

M.p. 141°–142° C.

NMR (CDCl$_3$) δ: 3.0–3.2 (2H, m), 3.4 (3H, s), 3.3–3.6 (4H, m), 4.0 4.2 (3H, m), 10.0 (2H, br).

Elementary analysis for C$_6$H$_{13}$NO$_2$.HCl:
Calcd. (%): C,42.99; H,8.42; N,8.36
Found (%): C,42.95; H,8.39; N,8.34.
[α]$_D^{20}$ +1.9° (c=1.0, CH$_3$OH).

REFERENCE EXAMPLE 13

Preparation of 2-fluoromethylmorpholine hydrochloride [compound (IX) in which R$^1$ is fluorine atom, hydrochloride thereof]

2-Fluoromethylmorpholine is prepared by the following two steps.

(1) N-Benzyl-2-fluoromethylmorpholine hydrochloride [compound (XII-1) in which R$^6$ is fluorine atom[:

A mixture of N-benzylethanolamine (10 g) and epifluorohydrin (10 g) is stirred at 45° C. for 3 hours and thereafter the excess epifluorohydrin is distilled off under reduced pressure. To the obtained oily substance is added conc. sulfuric acid (20 ml), and the mixture is stirred at 150° C. for one hour. The reaction mixture is allowed to cool and then poured into ice water. The solution is made basic by adding aqueous sodium hydroxide and extracted with toluene. The extract is washed with saline solution, dried over anhydrous magnesium sulfate and distilled under reduced pressure to remove the solvent. To the obtained oily substance is added 4N hydrogen chloride/ethyl acetate solution, and the precipitated solid substance is collected by filtration and washed with ether to give the title compound (8.9 g).

M.p. 160°–163° C.

NMR (D$_2$O) δ: 3.1–3.3 (2H, m), 3.5–3.6 (2H, m), 3.9–4.2 (3H, m), 4.4–4.7 (4H, m), 7.5 (5H, s).

Elementary analysis for C$_{12}$H$_{16}$NOF.HCl:
Calcd. (%): C,58.66; H,6.97; N,5.70
Found (%): C,58.45; H,6.82; N,5.63.

(2) 2-Fluoromethylmorpholine hydrochloride

To a solution of N-benzyl-2-fluoromethylmorpholine hydrochloride (1.46 g) in ethanol (85 ml) is added 10% palladium-carbon (0.2 g), and the mixture is stirred under hydrogen atmosphere (maximum hydrogen pressure: 6 kg/cm$^2$) at room temperature. After completion of absorption of hydrogen gas, palladium-carbon is filtered off, and the filtrate is concentrated under reduced pressure. To the residue are added ether (2 ml) and ethanol (0.5 ml), and the precipitated crystals are separated by filtration and dried under reduced pressure to give the title compound (0.6 g).

NMR (D$_2$O) δ: 3.1–3.5 (4H, m), 3.9–4.2 (3H, m), 4.5–4.7 (2H, m).

IR (KBr) ν$_{max}$ cm$^{-1}$: 2920, 1460, 1086, 1028.

REFERENCE EXAMPLE 14

Preparation of 2-methylmorpholine hydrochloride [compound (IX) in which R$^1$ is hydrogen atom, hydrochloride thereof]

2-Methylmorpholine hydrochloride is prepared by the following two steps.

(1) N-Benzyl-2-methylmorpholine [compound (XII-1) in which R$^6$ is hydrogen atom]:

A mixture of N-benzylethanolamine (14 g) and propylene oxide (16.1 g) is stirred at room temperature for 55.5 hours and thereafter the excess propylene oxide is distilled off under reduced pressure. To the resulting oily substance is added conc. sulfuric acid (30 ml), and the mixture is stirred at 145° C. for 30 minutes. The reaction mixture is allowed to cool and poured into ice water. The mixture is made basic by adding potassium hydroxide (150 g) and extracted with ethyl acetate. The extract is washed with saline solution and dried over anhydrous sodium sulfate. The solvent is distilled off under reduced pressure to give the title compound (12.5 g) as oily substance.

NMR (CDCl$_3$) δ: 1.1 (3H, d, J=6.5Hz), 1.6–2.9 (4H, m), 3.4 (2H, s), 3.4–4.0 (3H, m), 7.3 (5H, s).

(2) 2-Methylmorpholine hydrochloride:

N-Benzyl-2-methylmorpholine (6.5 g) and 10% palladium-carbon (1.1 g) are added to acetic acid (60 ml), and the mixture is stirred under hydrogen atmosphere (maximum hydrogen pressure: 6 kg/cm$^2$) at room temperature for 60 hours. Palladium-carbon is filtered off, and to the filtrate are added 4N hydrogen chloride/ethyl acetate solution (15 ml), and the mixture is concentrated under reduced pressure. To the concentrate is added toluene, and the mixture is evaporated to dryness. This procedure is repeated twice to give the title compound (4.6 g) as colorless powder.

NMR (D$_2$O) δ: 1.2 (3H, d, J=6.5Hz), 2.7–4.3 (7H, m).

REFERENCE EXAMPLE 15

Preparation of 2-chloromethylmorpholine hydrochloride [compound (IX) in which R$^1$ is chlorine atom, hydrochloride thereof]

N-Benzyl-2-chloromethylmorpholine prepared in the same manner as described in Synthetic Communication, Vol. 10 (1), pages 59–73, 1980 (1.5 g) is dissolved in 3N hydrogen chloride/ethanol (10 ml), and thereto is added 10% palladiumcarbon (330 mg), and the mixture is stirred under hydrogen pressure of 6 kg/cm$^2$ at room temperature. After completion of absorption of hydrogen gas, palladium-carbon is filtered off, and the filtrate is concentrated under reduced pressure. To the residue are added ether (2 ml) and ethanol (0.5 ml). The precipitated crystals are separated by filtration and dried under reduced pressure to give the title compound (1.4 g).

NMR (D$_2$O) δ: 2.9–3.1 (4H, m), 3.5–4.0 (5H, m).

REFERENCE EXAMPLE 16

Preparation of 2-hydroxymethylmorpholine hydrochloride [compound (IX) in which R$^1$ is hydroxy, hydrochloride thereof]

N-Benzyl-2-hydroxymethylmorpholine prepared in the same manner as described in Synthetic Communication, Vol. 10 (1), pages 59–73, 1980 (1.3 g) is subjected to hydrogenolysis in hydrogen chloride-containing ethanol in the same manner as described in Reference Example 15 to give 2-hydroxymethylmorpholine hydrochloride (1.3 g).

NMR (D$_2$O) δ: 3.0–3.2 (4H, m), 3.5–4.0 (5H, m).

REFERENCE EXAMPLE 17

Preparation of 2-methoxymethylmorpholine hydrochloride [compound (IX) in which $R^1$ is methoxy, hydrochloride thereof]

2-Methoxymethylmorpholine hydrochloride is prepared by the following two steps.

(1) 4-Benzyl-2-methoxymethylmorpholine:

To a sodium methoxide solution prepared from sodium (0.58 g) and anhydrous methanol (28 ml) are added N-benzyl-2-chloromethylmorpholine (cf Reference Example 15) (2.9 g) and sodium iodide (2.8 g), and the mixture is refluxed for 24 hours and thereafter stirred in a pressure vessel at 165°-170° C. for 23 hours. The solvent is distilled off under reduced pressure. To the residue is added chloroform, and the insoluble materials are filtered off. The fitrate is evaporated to dryness under reduced pressure, and the residue is purified by silica gel column chromatography (eluent, chloroform-methanol = 100:1) to give the title compound (1.05 g).

NMR (CDCl$_3$) δ: 2.0 (1H, t, J=11Hz), 2.2 (1H, dt, J=3Hz, J=11Hz), 2.6-2.8 (2H, m), 3.4 (3H, s), 3.3-3.5 (2H, m), 3.5 (2H, s), 3.7-3.8 (2H, m), 3.9-4.0 (1H, m), 7.2-7.4 (5H, m).

(2) 2-Methoxymethylmorpholine hydrochloride [compound (IX) in which $R^1$ is methoxy]:

N-Benzyl-2 methoxymethylmorpholine is subjected to hydrogenolysis in hydrogen chloride-containing ethanol in the same manner as described in Reference Example 15 to give 2-methoxymethylmorpholine hydrochloride.

NMR (D$_2$O) δ: 3.0-3.3 (2H, m), 3.3-3.4 (2H, m), 3.4 (3H, s), 3.5-3.7 (2H, m), 3.8-4.2 (3H, m).

REFERENCE EXAMPLE 18

Preparation of 2-hydroxymethyl-1-methylpiperazine diacetate [compound (X) in which $R^2$ is hydroxy and $R^3$ is methyl, diacetate thereof]

2-Hydroxymethyl-1-methylpiperazine diacetate is prepared by the following four steps.

(1) Ethyl 1-benzylpiperazine-3-carboxylate [compound (XV)]:

To a suspension of ethyl piperazine-2-carboxylate diacetate (35.0 g) in methylene chloride (400 ml) are added drowise a solution of 1,8-diazabicyclo[5.4.0]-7-undecene (60 ml) in methylene chloride (50 ml) and a solution of benzyl bromide (15.0 ml) in methylene chloride (50 ml) with stirring under ice cooling and thereafter the mixture is stirred at room temperature for 1.5 hour. The reaction mixture is washed twice with water (150 ml). The organic layer is dried over anhydrous magnesium sulfate and distilled under reduced pressure to remove the solvent. The residue is purified by silica gel column chromatography (eluent, chloroform-methanol = 50:1) to give the title compound (18.6 g).

Mass spectrum (m/e): 248 (M+).

NMR (CDCl$_3$) δ: 1.2 (3H, t, J=7Hz), 2.1 (1H, s), 2.2-2.3 (1H, m), 2.3-2.5 (1H, m), 2.5-2.6 (1H, m), 2.8-3.0 (2H, m), 3.0-3.1 (1H, m), 3.5 (1H, d, J=13Hz), 3.6 (1H, d, J=13Hz), 3.6 (1H, dd, J=3Hz, J=8Hz), 4.2 (2H, q, J=7Hz), 7.2-7.3 (5H, m).

(2) Ethyl 4-benzyl-1-methylpiperazine-2-carboxylate [compound (XVI) in which $R^3$ is methyl]:

To ethyl 4-benzylpiperazine-3-carboxylate (4.25 g) are added formalin (2.1 ml) and formic acid (0.97 ml) with stirring at room temperature, and the mixture is further stirred at 95°-100° C. for 30 minutes. The reaction mixture is diluted with water and adjusted to pH 11 by adding 1N aqueous sodium hydroxide and then extracted with chloroform (200 ml). The organic layer is washed with water, dried over anhydrous magnesium sulfate and distilled under reduced pressure to remove the solvent to give the title compound (4.45 g).

Mass spectrum (m/e): 262 (M+).

NMR (CDCl$_3$) δ: 1.2 (3H, t, J=7Hz), 2.3 (3H, s), 2.3-2.5 (3H, m), 2.6-2.7 (1H, m), 2.8-2.9 (1H, m), 2.9-3.0 (1H, m), 3.0 (1H, dd, J=3Hz, J=9Hz), 3.5 (1H, d, J=13Hz), 3.6 (1H, d, J=13Hz), 4.2 (2H, q, J=7Hz), 7.2-7.3 (5H, m).

(3) 4-Benzyl-2-hydroxymethyl-1-methylpiperazine [compound (XIV-1) in which $R^3$ is methyl]:

To a suspension of lithium aluminum hydride (0.98 g) in tetrahydrofuran (50 ml) is added dropwise a solution of ethyl 4-benzyl-1-methylpiperazine-2-carboxylate (4.54 g) in tetrahydrofuran (10 ml) with stirring at room temperature and thereafter the mixture is further stirred for 50 minutes. To the reaction mixture is added ice with stirring under ice cooling to decompose lithium aluminum hydride. The precipitated insoluble materials are filtered off. The filtrate is evaporated to dryness. The residue is dissolved in chloroform, dried over anhydrous sodium sulfate and distilled under reduced pressure to remove the solvent to give the title compound (2.95 g).

NMR (CDCl$_3$+D$_2$O) δ: 2.2-2.4 (2H, m), 2.3 (3H, s), 2.4-2.5 (1H, m), 2.6-2.8 (1H, m), 2.8-2.9 (1H, m), 2.5-3.2 (1H, br), 3.4 (1H, dd, J=2Hz, J=11Hz), 3.5 (2H, s), 3.9 (1H, dd, J=4Hz, J=11Hz), 7.2-7.3 (5H, m).

(4) 2-Hydroxymethyl-1-methylpiperazine diacetate [compound (X) in which $R^2$ is hydroxy and $R^3$ is methyl, diacetate thereof]:

To a solution of 4-benzyl-2-hydroxymethyl-1-methylpiperazine (0.90 g) in acetic acid (10 ml) is added 10% palladium-carbon (180 mg), and the mixture is stirred under hydrogen gas (5 kg/cm$^2$) at room temperature for 23 hours. Palladium-carbon is filtered off, and the filtrate is evaporated to dryness. To the residue is added ethanol (20 ml), and the mixture is evaporated to dryness. The residue is again dissolved in ethanol, and the solvent is distilled off under reduced pressure. This procedure is repeated four times to give the title compound (0.92 g).

NMR (CDCl$_3$) δ: 2.0 (6H, s), 2.5 (3H, s), 2.3-4.0 (10H, m), 8.2 (3H, s).

REFERENCE EXAMPLE 19

Preparation of 2-methoxymethyl-1-methylpiperazine dihydrochloride [compound (X) in which $R^2$ is methoxy and $R^3$ is methyl, dihydrochloride thereof]

2-Methoxymethyl-1-methylpiperazine dihydrochloride is prepared by the following three steps.

(1) 4-Benzyl-2-chloromethyl-1-methylpiperazine [compound (XIV-2) in which $R^3$ is methyl and $X^1$ is chlorine atom]:

4-Benzyl-2-hydroxymethyl-1-methylpiperazine (cf. Reference Example 18-(3)] (2 g) is dissolved in carbon tetrachloride (35 ml) and thereto is added dropwise thionyl chloride (1.33 ml) diluted with carbon tetrachloride (5 ml), and the mixture is stirred at 70° C. for one hour. The reaction mixture is allowed to cool till room temperature and is adjusted to pH 9 by adding 1N aqueous sodium hydroxide and then is extracted with chloroform. The organic layer is washed with water, dried over anhydrous sodium sulfate and the solvent is distilled off under reduced pressure. The residue is purified by silica gel column chromatography (eluent, chloroform-methanol=50:1) to give the title compound (1.13 g).

Mass spectrum (m/e): 238 (M+).

NMR (CDCl₃) δ: 2.3–2.5 (5H, m), 2.4 (3H, s), 2.6–2.7 (1H, m), 2.7–2.9 (2H, m), 3.5–3.6 (3H, m), 3.6 (1H, dd, J=6Hz, J=12Hz), 7.2–7.4 (5H, m).

(2) 4-Benzyl-2-methoxymethyl-1-methylpiperazine [compound (XIV-3) in which R³ is methyl]:

To a solution of sodium methoxide in methanol, which is prepared from sodium (0.24 g) and anhydrous methanol (50 ml), are added 4-benzyl-2-chloromethyl-1-methylpiperazine (1.2 g) and sodium iodide (0.9 g), and the mixture is stirred at 60°–65° C. for 16 hours. The solvent is distilled off under reduced pressure, and the resulting residue is dissolved in acetone and insoluble materials are filtered off. The filtrate is evaporated to dryness, and the residue is purified by silica gel column chromatography (eluent, chloroform-methanol=50:1) to give the title compound (1.0 g).

Mass spectrum (m/e): 234 (M+).

NMR (CDCl₃) δ: 2.1–2.4 (4H, m), 2.3 (3H, s), 2.7–2.9 (3H, m), 3.3 (3H, s), 3.3–3.4 (2H, m) 3 5 (1H, d J=13Hz), 3.51 (1H, d, J=13Hz), 7.2–7.4 (5H, m).

(3) 2-Methoxymethyl 1-methylpiperazine dihydrochloride [compound (X) in which R² is methoxy and R³ is methyl, dihydrochloride thereof]:

To a solution of 4-benzyl-2-methoxymethyl-1-methylpiperazine (0.95 g) in acetic acid (15 ml) is added 10% palladium-carbon (0.29 g), and the mixture is stirred under hydrogen gas (maximum hydrogen pressure: 5 kg/cm²) for 17 hours. Palladium-carbon is filtered off, and to the filtrate is added 2N hydrochloric acid (6 ml), and the mixture is evaporated to dryness under reduced pressure. To the residue is added ethanol (20 ml) and the mixture is evaporated to dryness under reduced pressure. This procedure is repeated five times to give the title compound (1.01 g).

NMR (D₂O) δ: 3.0 (3H, s), 3.4 (3H, s), 3.4–3.7 (4H, m), 3.7–3.9 (4H, m), 4.0 (1H, dd, J=3Hz, J=12Hz).

REFERENCE EXAMPLE 20

Preparation of 2-fluoromethyl-1-methylpiperazine dihydrochloride [compound (X) in which R² is fluorine atom and R³ is methyl, dihydrochloride thereof]:

2-Fluoromethyl-1-methylpiperazine dihydrochloride is prepared by the following two steps.

(1) 4-Benzyl-2-fluoromethyl-1-methylpiperazine [compound (XIV-4) in which R³ is methyl and X² is fluorine atom]:

A mixture of 4-benzyl-2-chloromethyl-1-methylpiperazine [cf. Reference Example 19-(1)] (2.14 g), potassium bifluoride (2.10 g) and ethylene glycol (20 ml) is stirred at 135° C. for 2 hours and 25 minutes. The reaction mixture is cooled till room temperature and adjusted to pH 9 by adding water and saturated aqueous sodium carbonate solution and then is extracted with ethyl acetate (300 ml). The organic layer is washed with water and thereto is added dilute hydrochloric acid, and the mixture is extracted with water (150 ml). The aqueous layer is washed with ethyl acetate and adjusted to pH 9 by adding saturated aqueous sodium carbonate solution and then extracted with ethyl acetate (300 ml). The organic layer is washed with water and saturated saline solution, dried over anhydrous magnesium sulfate and evaporated to dryness under reduced pressure. The residue is purified by silica gel column chromatography (eluent, firstly with chloroform, and then with chloroform-methanol=50:1) to give the title compound (0.19 g).

NMR (CDCl₃) δ: 2.1 (1H, t, J=10Hz), 2.4 (3H, d, J=1Hz), 2.2–2.6 (3H, m), 3.5 (2H, s), 4.4 (1H, ddd, J=4Hz, 10Hz, 48Hz), 4.5 (1H, ddd, J=4Hz, 10Hz, 48Hz), 7.2–7,4 (5H, m).

(2) 2-Fluoromethyl-1-methylpiperazine dihydrochloride [compound (X) in which R² is fluorine atom and R³ is methyl, dihydrochloride thereof]:

To a solution of 4-benzyl-2-fluoromethyl-1-methylpiperazine (0.2 g) in acetic acid (15 ml) is added 10% palladium-carbon (0.13 g), and the mixture is stirred under hydrogen gas (maximum hydrogen pressure: 5 kg/cm²) for 2 hours. The reaction mixture is filtered and to the filtrate is added 2N hydrochloric acid (1.5 ml), and the mixture is evaporated to dryness under reduced pressure. To the residue is added ethanol (10 ml) and the mixture is further evaporated to dryness. This procedure is repeated five times to give the title compound (0.17 g) as syrup.

REFERENCE EXAMPLE 21

Preparation of (6R)-1,8-diaza-4-oxabicyclo[4.4.0]-decane [compound (XI)]

(6R)-1,8-Diaza-4-oxabicyclo[4.4.0]decane is prepared by the following six steps.

(1) N-tert-Butyloxycarbonyl-L-serine benzylamide [compound (XVIII)]:

N-tert-Butyloxycarbonyl-L-serine (49.3 g) is dissolved in dichloromethane (400 ml) and thereto are added benzylamine (30.6 g) and 1-ethyl-3-(3-dimethylaminopropyl)carbodiimide hydrochloride (50.2 g) with stirring under ice cooling, and the mixture is further stirred at room temperature for 72 hours. The reaction mixture is washed with water, 0.5N hydrochloric acid, water and saturated aqueous sodium hydrogen carbonate solution in this order, dried over anhydrous sodium sulfate and distilled under reduced pressure to remove the solvent. The resulting solid is recrystallized from hexane-ethyl acetate to give the title compound (40.9 g).

M.p. 101°–103° C.

NMR (CDCl₃) δ: 1.4 (9H, s), 3.5–4.5 (6H, m), 5.8 (1H, d, J=6.5Hz), 7.0–7.4 (1H, m), 7.2 (5H, s).

(2) N-tert-Butyloxycarbonyl-O-carboxymethyl-L-serine benzylamide [compound (XIX)]:

N-tert-Butyloxycarbonyl-L-serine benzylamide (5.6 g) is dissolved in tetrahydrofuran and thereto are added bromoacetic acid (2.9 g) and potassium tert-butoxide (4.7 g) under ice cooling, and the mixture is stirred at room temperature for 72 hours. The solvent is distilled off under reduced pressure and to the residue is added 1% aqueous potassium hydroxide (50 ml), and the mixture is washed with chloroform (50 ml) three times. The aqueous layer is adjusted to pH 3.5 with 1N hydrochloric acid and extracted with chloroform (150 ml). The chloroform layer is washed with saturated aqueous saline solution, dried over anhydrous sodium sulfate and distilled under reduced pressure to remove the solvent. The resulting solid is washed with ether to give the title compound (5.7 g).

NMR (CDCl₃) δ: 1.4 (9H, s), 3.4–4.6 (7H, m), 6.3 (1H, m), 7.2 (5H, s), 7.5 (1H, m), 10.6 (1H, s).

(3) N-tert-Butyloxycarbonyl-O-methoxycarbonyl-methyl-L-serine benzylamide [compound (XX) in which R³ is methyl]:

N-tert-Butyloxycarbonyl-O-carboxymethyl-L-serine benzylamide (40.5 g) and methyl iodide (19.6 g) are dissolved in N,N-dimethylformamide (200 ml) and thereto is added potassium carbonate (9.5 g), and the mixture is stirred at room temperature for 2 hours. The solvent is distilled off under reduced pressure, and to the residue is added water (200 ml), and the mixture is extracted with chloroform (600 ml). The chloroform layer is washed with aqueous sodium thiosulfate and saturated aqueous saline solution in this order, dried over anhydrous sodium sulfate and the solvent is distilled off under reduced pressure to give the title compound (40 g) as oil.

NMR (CDCl₃) δ: 1.4 (9H, s), 3.7 (3H, s), 3.6–4.5 (5H, m), 4.1 (2H, s), 5.7 (1H, d, J=6.5Hz), 7.1 (1H, m), 7.3 (5H, s).

(4) (S)-N-Benzyl-5-oxo-3-morpholinecarboxamide [compound (XXI)]:

N-tert-Butyloxycarbonyl-O-methoxycarbonylmethyl-L-serine benzylamide (47 g) is dissolved in 4N hydrogen chloride/dioxane (100 ml) and the mixture is stirred under ice cooling for one hour. Thereafter, the solvent is distilled off under reduced pressure. To the residue is added methanol (50 ml), and the solvent is again distilled off under reduced pressure. The residue is dissolved in methanol (200 ml) and thereto is added potassium carbonate (15.4 g), and the mixture is stirred at room temperature for 20 hours. After completion of the reaction, insoluble materials are filtered off, and the solvent is distilled off under reduced pressure. To the residue is added water (50 ml), and the mixture is extracted with chloroform (600 ml). The chloroform layer is dried over anhydrous sodium sulfate, and distilled under reduced pressure to remove the solvent. The residue is recrystallized from ethanol to give the title compound (18 g).

M.p. 130°-133° C.

NMR (CDCl₃) δ: 3.8 (1H, dd, J=4Hz, J=12Hz), 3.9–4.0 (3H, m), 4.2 (1H, m), 4.4 (2H, d, J=3Hz), 7.2–7.3 (5H, m).

Elementary analysis for C₁₂H₁₄N₂O₃:
Calcd. (%): C,61.53; H,6.02; N,11.96
Found (%): C,61.37; H,5.93; N,11.96.

(5) (R)-N-Benzyl-N-(3-morpholinylmethyl)amine [compound (XXII)]:

To a suspension of (S)-N-benzyl-5 oxo-3-morpholine carboxamide (3.0 g) in toluene (30 ml) is added drowise sodium bis(2-methoxyethoxy)aluminum hydride (20 g) under ice cooling, and the mixture is stirred at room temperature for 20 hours. To the reaction mixture is added water while keeping the temperature at lower than 20° C., and the precipitated insoluble materials are filtered off. The filtrate toluene layer is separated, dried over anhydrous sodium sulfate and distilled under reduced pressure to remove the solvent to give the title compound (2.0 g) as oil.

NMR (CDCl₃) δ: 2.4–3.9 (9H, m), 3.8 (2H, s), 7.2 (5H, s).

(6) (6R) N Benzyl-1,8-diaza-4-oxabicyclo[4.4.0]-decane [compound (XXIII)]:

(R)-N-Benzyl-N-(3-morpholinylmethyl)amine (1.0 g) is dissolved in N,N-dimethylformamide (10 ml) and thereto are added potassium carbonate (0.67 g) and 1,2-dibromoethane (1.0 g), and the mixture is stirred at 50° C. for 16 hours. N,N-Dimethylformamide is distilled off under reduced pressure, and to the residue is added water (10 ml) and the mixture is adjusted to pH 2.0 with 3N hydrochloric acid. The aqueous layer is washed twice with ethyl acetate, adjusted to pH 8.0 with saturated aqueous potassium hydrogen carbonate solution and then extracted with ethyl acetate (50 ml). The extract is dried over anhydrous sodium sulfate and distilled under reduced pressure to remove the solvent to give the title compound (0.7 g) as oil.

NMR (CDCl₃) δ: 2.1–3.8 (13H, m), 3.5 (2H, s), 7.3 (5H, s).

(7) (6R)-1.8-Diaza-4-oxabicyclo[4.4.0]decane [compound (XI)]:

(6R)-N-Benzyl-1,8-diaza-4-oxabicyclo[4.4.0]decane (0.7 g) is dissolved in ethanol, and thereto is added 10% palladium-carbon (80 mg), and the mixture is subjected to hydrogenolysis (maximum hydrogen pressure: 6 kg/cm²). After completion of absorption of hydrogen gas, the catalyst is filtered off, and the solvent is distilled off under reduced pressure to give the title compound (0.4 g) as oil.

NMR (CDCl₃) δ: 2.3–3.8 (13H, m).

REFERENCE EXAMPLE 22

Preparation of 2-ethoxymethylmorpholine [compound (IX) in which R¹ is ethoxy]

2-Ethoxymethylmorpholine is prepared by the following two steps.

(1) 4-Benzyl-2-ethoxymethylmorpholine:

4-Benzyl-2-(p-toluenesulfonyloxymethyl)morpholine hydrochloride [cf. Reference Example 11-(1)] (3 g) and sodium ethoxide (2 g) are added to ethanol (150 ml), and the mixture is stirred at 70° C. for 24 hours. The reaction mixture is concentrated under reduced pressure, and to the residue is added saturated aqueous sodium hydrogen carbonate, and the mixture is extracted with ethyl acetate. The extract is washed with saturated aqueous sodium hydrogen carbonate solution, dried over anhydrous magnesium sulfate and distilled under reduced pressure to remove the solvent. The residue is purified by silica gel column chromatography (eluted by chloroform-methanol=40:1) and further subjected to bulb-to-bulb distillation (at 162° C., 0.4 mmHg) to give the title compound (0.9 g) as colorless liquid.

NMR (CDCl₃) δ: 1.2 (3H, t, J=7Hz), 1.9 (1H, dd, J=11Hz, J=10.5Hz), 2.2 (1H, td, J=11Hz, J=3Hz), 2.6–2.7 (1H, m), 2.8 (1H, dt, J=11Hz, J=2Hz), 3.3–3.5 (6H, m), 3.6–3.8 (2H, m), 3.8–3.9 (1H, m), 7.2–7.4 (5H, m).

(2) 2-Ethoxymethylmorpholine:

4-Benzyl-2-ethoxymethylmorpholine (1.6 g) and 10% palladium-carbon (200 mg) are added to ethanol (30 ml), and the mixture is stirred under hydrogen pressure of 5 kg/cm² for 24 hours. Palladium-carbon is filtered off, and the solvent is distilled off under reduced pressure to give the title compound (0.7 g) as colorless liquid.

NMR (CDCl₃) δ: 1.2 (3H, t, J=7Hz), 3.0–3.2 (2H, m), 3.4–3.6 (6H, m), 4.0–4.2 (3H, m), 8.2 (1H, br).

REFERENCE EXAMPLE 23

Preparation of 2-benzoyloxymethylmorpholine hydrochloride

2-Benzoyloxymethylmorpholine hydrochloride is prepared by the following two steps.

(1) 4-Benzyl-2-benzoyloxymethylmorpholine hydrochloride:

4-Benzyl-2-hydroxymethylmorpholine (prepared by the method disclosed in Synthetic Communication, Vol. 10, pages 59-73, 1980) (200 g) and triethylamine (122 g) are dissolved in chloroform (1.5 liter), and thereto is added dropwise benzoyl chloride (135 g) with stirring under ice cooling. The mixture is stirred at room temperature for 16 hours and thereafter to the mixture is added water. The chloroform layer is separated, washed with saturated aqueous sodium hydrogen carbonate solution and saturated aqueous saline solution in this order, dried over anhydrous magnesium sulfate and distilled under reduced pressure to remove the solvent. The residue is dissolved in ethyl acetate (150 ml) and thereto is added 4N hydrogen chloride/ethyl acetate (250 ml) with stirring under ice cooling, and the precipitated crystals are separated by filtration, washed with ethyl acetate and acetone in this order to give the title compound (240 g) as colorless crystals.

M.p. 168° C.

NMR (DMSO-$d_6$) δ: 3.0-3.3 (3H, m), 3.4-3.5 (1H, m), 3.9-4.1 (2H, m), 4.3-4.5 (5H, m), 7.4-7.5 (3H, m), 7.5-7.6 (2H, m), 7.6-7.7 (3H, m), 8.0 (2H, m), 11.9 (1H, bs).

Elementary analysis for $C_{19}H_{21}NO_3 \cdot HCl \cdot \frac{1}{4}H_2O$:
Calcd. (%): C,63.95; H,6.50; N,3.93
Found (%): C,63.95; H,6.76; N,4.00.

(2) 2-Benzoyloxymethylmorpholine hydrochloride:

10% Palladium-carbon (40 g) and 4-benzyl-2-benzoyloxymethylmorpholine hydrochloride (202 g) are added to a mixture of ethanol (600 ml) and water (200 ml), and the mixture is stirred under hydrogen pressure of 10 kg/cm$^2$ at 40° C. for 5 hours. Palladium-carbon is filtered off, and the solvent is distilled off under reduced pressure. To the residue is added ethanol, and the mixture is distilled under reduced pressure. This procedure is repeated three times. The resulting crystals are washed with ether and recrystallized from chloroform-ethanol to give the title compound (91 g) as colorless crystals.

M.p. 196° C.

NMR (DMSO-$d_6$) δ: 2.9-3.1 (2H, m), 3.1-3.2 (1H, m), 3.3-3.4 (1H, m), 3.8 (1H, td, J=12Hz, J=2Hz), 4.0 (1H, dd, J=12.5 Hz, J=3Hz), 4.1-4.2 (1H, m), 4.3-4.4 (2H, m), 7.5-7.6 (2H, m), 7.7 (1H, m). 8.0 (2H, m), 9.7 (2H, br).

Elementary analysis for $C_{12}H_{15}NO_3 \cdot HCl \cdot \frac{1}{4}H_2O$:
Calcd. (%): C,54.97; H,6.34; N,5.34
Found (%): C,54.89; H,6.31; N,5.30.

REFERENCE EXAMPLE 24

Preparation of (2S)-2-benzoyloxymethylmorpholine hydrochloride (2S)-2-Benzoyloxymethylmorpholine hydrochloride is prepared by the following two steps.

(1) (2S)-4-Benzyl-2-benzoyloxymethylmorpholine hydrochloride:

(2S)-4-Benzyl-2-(p-toluenesulfonyloxymethyl)-morpholine.N-(p-toluenesulfonyl)-L-glutamic acid salt [cf. Reference Example 11-(2)] (16.0 g) is added to an excess amount of aqueous sodium hydroxide solution, and the mixture is extracted with chloroform. The extract is dried over anhydrous magnesium sulfate and distilled under reduced pressure to remove the solvent. The obtained residue is dissolved in N,N-dimethylformamide (80 ml) and thereto are added benzoic acid (5.9 g) and potassium carbonate (6.7 g), and the mixture is stirred at 150° C. for 2 hours. The reaction mixture is poured into ice water and extracted with chloroform. The extract is washed with saturated aqueous saline solution, dried over anhydrous magnesium sulfate and distilled under reduced pressure to remove the solvent. The obtained residue is dissolved in acetone (10 ml) and thereto is added 4N hydrogen chloride/ethyl acetate (10 ml). The pricipitate is separated by filtration and recrystallized from ethyl acetate-ethanol to give the title compound (4.3 g).

M.p. 214°-217° C.

NMR (DMSO-$d_6$) δ: 3.0-3.3 (3H, m), 3.4-3.5 (1H, m), 4.0 (2H, d, J=7Hz), 4.3-4.5 (5H, m), 7.4-7.5 (3H, m), 7.5-7.6 (2H, m), 7.7 (3H, m), 8.0 (2H, m), 12.1 (1H, bs).

Elementary analysis for $C_{19}H_{21}NO_3 \cdot HCl$:
Calcd. (%): C,65.61; H,6.37; N,4.03
Found (%): C,65.54; H,6.31; N,3.97.
$[\alpha]_D^{21}$ +22.7° (c=1.0, CH$_3$OH).

(2) (2S)-2-Benzoyloxymethylmorpholine hydrochloride:

(2S)-4-Benzyl-2-benzoyloxymethylmorpholine hydrochloride (4.0 g) is dissolved in methanol (32 ml) and thereto is added 10% palladium-carbon (0.8 g), and the mixture is stirred under hydrogen pressure of 5 kg/cm$^2$ at room temperature for 4 hours. Palladium-carbon is filtered off and the solvent is distilled off under reduced pressure. The residue is recrystallized from chloroform-ethanol to give the title compound (1.25 g).

M.p. 170°-171° C.

NMR (D$_2$O) δ: 3.2-3.3 (2H, m), 3.4 (1H, m), 3.5-3.6 (1H, m), 3.9-4.0 (1H, m), 4.2-4.3 (2H, m), 4.4 (1H, dd, J=5Hz, J=12Hz), 4.6 (1H, dd, J=3Hz, J=12Hz), 7.5-7.6 (2H, m), 7.7-7.8 (1H, m), 8.0-8.1 (2H, m).

Elementary analysis for $C_{12}H_{15}NO_3 \cdot HCl$:
Calcd. (%): C,55.93; H,6.26; N,5.43.
Found (%): C,55.94; H,6.12; N,5.39.

REFERENCE EXAMPLE 25

Preparation of (2R)-2-benzoyloxymethylmorpholine hydrochloride (2R)-2-Benzoyloxymethylmorpholine hydrochloride is prepared by the following two steps.

(1) (2R)-4-Benzyl-2-benzoyloxymethylmorpholine hydrochloride:

In the same manner as described in Reference Example 24-(1) except that (2R)-4-benzyl-2-(p-toluenesulfonyloxymethyl)morpholine.N-(p-toluenesulfonyl)-D-glutamic acid salt [cf. Reference Example 12-(1)] is used instead of (2S)-4-benzyl-2-(p-toluenesulfonyloxymethyl)-morpholine.N-(p-toluenesulfonyl)-L-glutamic acid salt, there is prepared the title compound.

M.p. 214°-215° C.

NMR (DMSO-$d_6$) δ: 3.0-3.3 (3H, m), 3.4-3.5 (1H, m), 4.0 (2H, d, J=7Hz), 4.3-4.5 (5H, m), 7.4-7.5 (3H, m), 7.5-7.6 (2H, m), 7.7 (3H, m), 8.0 (2H, m), 12.1 (1H, bs).

Elementary analysis for $C_{19}H_{21}NO_3 \cdot HCl$:
Calcd. (%): C,65.61; H,6.37; N,4.03
Found (%): C,65.49; H,6.39; N,3.96.
$[\alpha]_D^{21}$ −23.2° (c=1.0, CH$_3$OH).

(2) (2R)-2-Benzoyloxymethylmorpholine hydrochloride:

In the same manner as described in Reference Example 24-(2) except that (2R)-4-benzyl-2-benzoyloxymethylmorpholine hydrochloride is used instead of (2S)-4-benzyl-2-benzoyloxymethylmorpholine hydrochloride, there is prepared the title compound.

M.p. 170°-171° C.

NMR (DMSO-$d_6$) δ: 2.9-3.1 (2H, m), 3.1-3.2 (1H, m), 3.3-3.4 (1H, m), 3.8-3.9 (1H, m), 4.0 (1H, m), 4.1-4.2

(1H, m), 4.3–4.4 (2H, m), 7.5–7.6 (2H, m), 7.7 (1H, m), 8.0 (2H, m), 9.8 (2H, bs).

Elementary analysis for $C_{12}H_{15}NO_3 \cdot HCl$:
Calcd (%): C,55.93; H,6.26; N,5.43
Found (%): C,55.88; H,6.18; N,5.41.

EXAMPLE 1

Preparation of 9,1-(methylimino)methano-7-fluoro-8-(2-methylmorpholino)-5-oxo-5H-thiazolo[3,2-a]quinoline-4-carboxylic acid [compound (I) in which Z is 2-methylmorpholino]

Diacetoxy [9,1-(methylimino)methano-7,8-difluoro-5-oxo-5H-thiazolo[3,2-a]quinoline-4-carboxy]borane (cf. Example 25 hereinafter) (0.75 g) is added to a mixture of dimethylsulfoxide (30 ml), 2-methylmorpholine hydrochloride (cf. Reference Example 14) (0.4 g) and triethylamine (0.8 g), and the mixture is stirred at 80° C. for 15 hours. Dimethylsulfoxide is distilled off under reduced pressure, and the residue is washed with isopropyl ether and acetonitrile in this order, and thereto are added acetone (50 ml), water (10 ml) and conc. hydrochloric acid (5 ml). The mixture is stirred at room temperature for 2 hours. The resulting solid is washed with water and ethanol in this order and recrystallized from acetonitrile-ethanol to give the title compound (0.42 g).

M.p. decomposed at around 256° C.

NMR (DMSO-d$_6$) δ: 1.1 (3H, d, J=6Hz), 2.8 (3H, s), 2.9 3.0 (1H, m), 3.2–3.5 (3H, m), 3.7–3.8 (2H, m), 3.8–3.9 (1H, m), 4.5 (2H, s), 7.6 (1H, s), 7.6 (1H, d, J=12.5Hz), 15.8 (1H, s).

IR (KBr) $\nu_{max}$ cm$^{-1}$: 1691, 1614, 1463.

Elementary analysis for $C_{19}H_{18}N_3O_4SF$:
Calcd. (%): C,56.57; H,4.50; N,10.42
Found (%): C,56.48; H,4.64; N,10.33.

EXAMPLE 2

Preparation of 9,1-(methylimino)methano-7-fluoro-8-(2-hydroxymethylmorpholino)-5-oxo-5H-thiazolo[3,2-a]-quinoline-4-carboxylic acid [compound (I) in which Z is 2-hydroxymethylmorpholino]

Diacetoxy [9,1-(methylimino)methano-7,8-difluoro-5-oxo-5H-thiazolo[3,2-a]quinoline-4-carboxy]borane (cf. Example 25 hereinafter) (2 g) is added to a mixture of dimethylsulfoxide (20 ml), 2-hydroxymethylmorpholine hydrochloride (cf. Reference Example 16) (1.5 g) and triethylamine (3.6 g), and the mixture is stirred at 60° C. for 15 hours. Dimethylsulfoxide is distilled off under reduced pressure, and to the residue are added acetone (5 ml), conc. hydrochloric acid (5 ml) and water (10 ml). The mixture is stirred at 60° C. for one hour. The resulting solid is washed with water and ethanol in this order and recrystallized from chloroform - ethanol to give the title compound (0.8 g).

M.p. decomposed at around 257° C.

NMR (DMSO-d$_6$) δ: 2.8 (3H, s), 3.0–3.1 (1H, m), 3.2–3.8 (7H, m), 3.9–4.0 (1H, m), 4.5 (2H, s), 4.8 (1H, t, J=5.5Hz), 7.6 (1H, s), 7.6 (1H, d, J=12.5Hz), 15.8 (1H, s).

IR (KBr) $\nu_{max}$ cm$^{-1}$: 1696, 1614, 1472, 1452, 1404.

Elementary analysis for $C_{19}H_{18}N_3O_5SF$:
Calcd. (%): C,54.41; H,4.33; N,10.02
Found (%): C,54.22; H,4.30; N,9.93.

EXAMPLE 3

Preparation of 9,1-(methylimino)methano-7-fluoro-8-(2-fluoromethylmorpholino)-5-oxo-5H-thiazolo[3,2-a]-quinoline-4-carboxylic acid [compound (I) in which Z is 2-fluoromethylmorpholino]

Diacetoxy [9,1-(methylimino)methano-7,8-difluoro-5-oxo-5H-thiazolo[3,2-a]quinoline-4-carboxy]borane (cf. Example 25 hereinafter) (3 g) is added to a mixture of dimethylsulfoxide (60 ml), 2-fluoromethylmorpholine hydrochloride (cf. Reference Example 13) (3 g) and triethylamine (4.8 g), and the mixture is stirred at 70° C. for 6 hours. Dimethylsulfoxide is distilled off under reduced pressure, and to the residue are added acetone (9 ml), conc. hydrochloric acid (9 ml) and water (15 ml). The mixture is stirred at 50° C. for 6 hours. The resulting solid is washed with water and recrystallized from acetonitrile-ethanol to give the title compound (1.3 g).

M.p. decomposed at around 245° C.

NMR (DMSO-d$_6$) δ: 2.8 (3H, s), 3.1–3.3 (2H, m), 3.4–3.5 (2H, m), 3.7–4.0 (3H, m), 4.5 (2H, s), 4.5 (2H, dd, J=4Hz, J=47Hz), 7.6 (1H, s), 7.6 (1H, d, J=12.5Hz), 15.8 (1H, s).

IR (KBr) $\nu_{max}$ cm$^{-1}$: 1694, 1614, 1468.

Elementary analysis for $C_{19}H_{17}N_3O_4SF_2$:
Calcd. (%): C,54.15; H,4.06; N,9.97
Found (%): C,54.06; H,4.07; N,9.98.

EXAMPLE 4

Preparation of 9,1-(methylimino)methano-7-fluoro-8-(2-chloromethylmorpholino)-5-oxo-5H-thiazolo[3,2-a]-quinoline-4-carboxylic acid [compound (I) in which Z is 2-chloromethylmorpholino]

Diacetoxy [9,1-(methylimino)methano-7,8-difluoro-5-oxo-5H-thiazolo[3,2-a]quinoline-4-carboxy]borane (cf. Example 25 hereinafter) (1 g) is added to a mixture of dimethylsulfoxide (50 ml), 2-chloromethylmorpholine hydrochloride (cf. Reference Example 15) (1.2 g) and triethylamine (1.6 g), and the mixture is stirred at 70° C. for 6 hours. Dimethylsulfoxide is distilled off under reduced pressure, and to the residue are added acetone (5 ml), conc. hydrochloric acid (3 ml) and water (10 ml). The mixture is stirred at 50° C. for one hour. The resulting solid is washed with water and ethanol in this order and recrystallized from chloroform-methanol to give the title compound (0.1 g).

M.p. decomposed at around 250° C.

NMR (DMSO-d$_6$) δ: 2.8 (3H, s), 3.1–3.3 (2H, m), 3.4–3.5 (1H m) 3.5–3.6 (1H, m), 3.7–3.9 (4H, m), 4 0–4 1 (1H, m), 4.5 (2H, s), 7.6 (1H, s), 7.6 (1H, d, J=12.5Hz), 15.8 (1H, s).

IR (KBr) $\nu_{max}$ cm$^{-1}$: 1694, 1614, 1488.

Elementary analysis for $C_{19}H_{17}N_3O_4SFCl$:
Calcd. (%): C,52.12; H,3.91; N,9.60
Found (%): C,52.23; H,4.02; N,9.59.

EXAMPLE 5

Preparation of 9,1-(methylimino)methano-7-fluoro-8-(2-methoxymethylmorpholino)-5-oxo-5H-thiazolo[3,2-a]-quinoline-4-carboxylic acid [compound (I) in which Z is 2-methoxymethylmorpholino]

Diacetoxy [9,1-(methylimino)methano-7,8-difluoro-5-oxo-5H-thiazolo[3,2-a]quinoline-4-carboxy]borane (cf. Example 25 hereinafter) (0.9 g) is added to a mixture of dimethylsulfoxide (20 ml), 2-methoxymethylmorpholine hydrochloride (cf. Reference Example 17) (0.8 g) and triethylamine (5.1 g), and the mixture is stirred at 60° C. for 22 hours. Dimethylsulfoxide is distilled off under reduced pressure, and to the residue are added acetone (15 ml), conc. hydrochloric acid (5 ml) and water (40 ml). The mixture is stirred at room temperature for one hour. The resulting solid is washed with water and acetone in this order and recrystallized from acetonitrile to give the title compound (0.54 g).

M.p. decomposed at around 224° C.

NMR (CDCl$_3$) δ: 2.9 (3H, s), 3.3 (1H, ddd, J=2.5Hz, J=10.5Hz, J=12.5Hz), 3.4 (3H, s), 3.4–3.6 (5H, m), 3.8–4.0 (2H, m), 4.0 (1H, dt, J=2Hz, J=11Hz), 4.4 (2H, s), 7.0 (1H, s), 7.6 (1H, d, J=12.5Hz), 15.4 (1H, bs).

IR (KBr) $\nu_{max}$ cm$^{-1}$: 1696, 1616, 1490.

Elementary analysis for C$_{20}$H$_{20}$N$_3$O$_5$SF.$\frac{1}{4}$H$_2$O:

Calcd. (%): C,54.85; H,4.72; N,9.59

Found (%): C,54.90; H,4.73; N,9.59.

EXAMPLE 6

Preparation of 9,1-(methylimino)methano-7-fluoro-8-(2-methylmorpholino)-5-oxo-5H-thiazolo[3,2-a]quinoline-4-carboxylic acid [compound (I) in which Z is 2-methylmorpholino]

This compound is prepared by the following two steps.

(1) Difluoro [9,1-(methylimino)methano-7-fluoro-8-(2-methylmorpholino)-5-oxo-5H-thiazolo[3,2-a]quinoline-4-carboxy]borane:

To a mixture of difluoro [9,1-(methylimino)methano-7,8-difluoro-5-oxo-5H-thiazolo[3,2-a]quinoline-4-carboxy]-borane (cf. Example 27 hereinafter) (0.75 g), 2-methylmorpholine hydrochloride (cf. Reference Example 14) (0.42 g) and dimethylsulfoxide (50 ml) is added triethylamine (1.0 g), and the mixture is stirred at 80° C. for 20 hours. The reaction mixture is concentrated to dryness under reduced pressure, and to the residue are added acetonitrile (10 ml) and isopropyl ether (20 ml), and the insoluble materials are separated by filtration, washed with isopropyl ether, water and acetonitrile in this order to give the title compound (0.8 g).

M.p. above 280° C.

NMR (DMSO-d$_6$) δ: 1.1 (3H, d, J=6Hz), 2.8 (3H, s), 2.9–3.1 (1H, m), 3.2–3.4 (1H, m), 3.5–3.6 (2H, m), 3.7–3.8 (2H, m), 3.9–4.0 (1H, m), 4.6 (2H, s), 7.9 (1H, d, J=12.5Hz), 8.0 (1H, s).

IR (KBr) $\nu_{max}$ cm$^{-1}$: 1687, 1513, 1483, 1441.

Elementary analysis for C$_{19}$H$_{17}$N$_3$O$_4$SF$_3$B.$\frac{1}{4}$H$_2$O:

Calcd. (%): C,49.58; H,3.94; N,9.13

Found (%): C,49.62; H,3.98; N,9.02.

(2) 9,1-(Methylimino)methano-7-fluoro-8-(2-methylmorpholino)-5-oxo-5H-thiazolo[3,2-a]quinoline-4-carboxylic acid:

To a solution of sodium hydroxide (0.18 g) in water (3 ml) are added difluoro [9,1-(methylimino)methano-7-fluoro-8-(2-methylmorpholino)-5-oxo-5H-thiazolo[3,2-a]-quinoline-4-carboxy]borane (0.45 g) and ethanol (15 ml), and the mixture is refluxed for 30 minutes. After allowing to cool, acetic acid (1 ml) and water (50 ml) are added to the mixture, and the precipitated crystals are separated by filtration and washed with water and ethanol in this order and recrystallized from acetonitrile-ethanol to give the title compound (0.28 g). The obtained compound is identical with 9,1-(methylimino)-methano-7-fluoro-8-(2-methylmorpholino)-5-oxo-5H-thiazolo[3,2-a]quinoline-4-carboxylic acid obtained in Example 1 in the physical properties thereof.

EXAMPLE 7

Preparation of 9,1-(methylimino)methano-7-fluoro-8-[(6R)-1,8-diaza-4-oxabicyclo[4.4.0]deca-8-yl]-5-oxo-5H-thiazolo[3,2-a]quinoline-4-carboxylic acid [compound (I) in which Z is (6R)-1,8-diaza-4-oxabicyclo[4.4.0]deca-8-yl]

Diacetoxy [9,1-(methylimino)methano-7,8-difluoro-5-oxo-5H-thiazolo[3,2-a]quinoline 4-carboxy]borane (cf. Example 25 hereinafter) (0.8 g) is added to a mixture of dimethylsulfoxide (10 ml), (6R)-1,8-diaza-4-oxabicyclo-[4.4.0]decane (cf. Reference Example 21) (0.33 g) and triethylamine (1.5 g), and the mixture is stirred at 60° C. for 5 hours. Dimethylsulfoxide is distilled off under reduced pressure, and to the residue are added acetone (5 ml), conc. hydrochloric acid (3 ml) and water (10 ml). The mixture is stirred at 50° C. for one hour. The reaction mixture is concentrated until half volume, and thereto is added water (10 ml), and the insoluble materials are filtered off. The filtrate is washed with chloroform and adjusted to pH 7.5 with aqueous sodium hydroxide, and the precipitated crystals are extracted with chloroform-methanol (30:1 v/v). The extract is dried over anhydrous sodium sulfate and concentrated. The residue is recrystallized from chloroform-ethanol to give the title compound (0.11 g).

M.p. above 300° C.

NMR (DMSO-d$_6$) δ: 2.2–2.5 (4H, m), 2.7–3.0 (3H, m), 2.8 (3H, s), 3.1–3.4 (2H, m), 3.5–3.8 (4H, m), 4.5 (2H, s), 7.6 (1H, s), 7.7 (1H, d, J=12.5Hz), 15.8 (1H, s).

Elementary analysis for C$_{21}$H$_{21}$N$_4$O$_4$SF:

Calcd. (%): C,56.75; H,4.76; N,12.60

Found (%): C,56.71; H,4.89; N,12.49.

EXAMPLE 8

Preparation of 9,1-(methylimino)methano-7-fluoro-8-(4-oxopiperidino)-5-oxo-5H-thiazolo[3,2-a]quinoline-4-carboxylic acid [compound (I) in which Z is 4-oxopiperidino]

4-Piperidone hydrochloride monohydrate (0.5 g) is dissolved in dimethylsulfoxide (3 ml) and thereto are added diacetoxy [9,1-(methylimino)methano-7,8-difluoro-5-oxo-5H-thiazolo[3,2-a]quinoline-4-carboxy]-borane (cf. Example 25 hereinafter) (0.5 g) and triethylamine (1.6 ml), and the mixture is stirred at 60° C. for 5 hours. Triethylamine (1 ml) is additionally added thereto, and the mixture is further stirred at the same temperature overnight. The solvent is distilled off under reduced pressure, and to the residue are added acetone (5 ml), water (10 ml) and conc. hydrochloric acid (3 ml), and the mixture is stirred at room temperature for one hour. The resulting solid is separated by filtration, washed with water, acetonitrile and ether in this order to give the title compound (0.36 g). This product is recrystallized from acetonitrile-dimethylsulfoxide to give a product having the following physical properties.

M.p. decomposed at around 290° C.

NMR (DMSO-d$_6$) δ: 2.5–2.6 (4H, m), 2.8 (3H, s), 3.6–3.7 (4H, m), 4.5 (2H, s), 7.6 (1H, s), 7.7 (1H, d, J=12.5Hz), 15.9 (1H, s).

IR (KBr) $\nu_{max}$ cm$^{-1}$: 1696, 1612, 1582, 1462.

Elementary analysis for C$_{19}$H$_{16}$N$_3$O$_4$SF.$\frac{1}{4}$H$_2$O:

Calcd. (%): C,56.22; H,4.10; N,10.35
Found (%): C,56.22; H,4.11; N,10.36.

EXAMPLE 9

Preparation of 9,1-(methylimino)methano-7-fluoro-8-(4-dimethylaminopiperidino)-5-oxo-5H-thiazolo[3,2-a]quinoline-4-carboxylic acid [compound (I) in which Z is 4-dimethylaminopiperidino]

A mixture of diacetoxy [9,1-(methylimino)methano-7,8-difluoro-5-oxo-5H-thiazolo[3,2-a]quinoline-4-carboxyl]-borane (cf. Example 25 hereinafter) (0.64 g), 4-dimethylaminopiperidine dihydrochloride (cf. J. Chem. Soc., 3165, 1957) (0.86 g), triethylamine (1.4 g) and dimethylsulfoxide (10 ml) is stirred at 60° C. for 2 hours. The reaction mixture is concentrated to dryness under reduced pressure, and to the residue is added 2N hydrochloric acid (8 ml), and the mixture is stirred at room temperature for one hour. The precipitated crystal is separated by filtration, washed with 2N hydrochloric acid and acetone and then dissolved in water (20 ml). The mixture is adjusted to pH 9.0 by adding aqueous sodium hydroxide. The precipitated product is separated by filtration, washed with water, dried, and then recrystallized from chloroform-methanol to give the title compound (0.24 g).

M.p. decomposed at around 238° C.

NMR (DMSO-$d_6$) δ: 1.5–1.6 (2H, m), 1.8–1.9 (2H, m), 2.2 (6H, s), 2.2–2.4 (1H, m), 2.8 (3H, s), 3.1–3.2 (2H, m), 3.6–3.7 (2H, m), 4.5 (2H, s), 7.5 (1H, s), 7.5 (1H, d, J=12.5Hz), 15.7 (1H, bs).

IR (KBr) $\nu_{max}$ cm$^{-1}$: 1710, 1614, 1492, 1460.

Elementary analysis for $C_{21}H_{23}N_4O_3SF$:

Calcd. (%): C,58.59; H,5.39; N,13.01
Found (%): C,58.44; H,5.40; N,13.13.

EXAMPLE 10

Preparation of 9,1-(methylimino)methano-7-fluoro-8-(3-hydroxymethyl-4-methyl-1-piperazinyl)-5-oxo-5H-thiazolo[3,2-a]quinoline-4-carboxylic acid hydrochloride [compound (I) in which Z is 3-hydroxymethyl-4-methyl-1-piperazinyl, hydrochloride thereof]

A mixture of diacetoxy [9,1-(methylimino)methano-7,8-difluoro-5-oxo-5H-thiazolo[3,2-a]quinoline-4-carboxyl]-borane (cf. Example 25 hereinafter) (0.87 g), 2-hydroxymethyl-1-methylpiperazine diacetate (cf. Reference Example 18) (0.92 g), triethylamine (3.25 ml) and dimethylsulfoxide (16 ml) is stirred at 60° C. for 4 hours. The reaction mixture is concentrated to dryness under reduced pressure, and to the residue is added 2N hydrochloric acid (7 ml) and acetone (14 ml), and the mixture is stirred at room temperature for 30 minutes. The precipitated crystal is separated by filtration, washed with 2N hydrochloric acid and acetone. The precipitated crystal is recrystallized from 2N hydrochloric acid-methanol to give the title compound (0.45 g).

M.p. decomposed at around 270° C.

NMR (DMSO-$d_6$+$D_2O$) δ: 2.8 (3H, s), 3.0 (3H, s), 2.3–4.1 (9H, m), 4.5 (2H, s), 7.5 (1H, d, J=12.5Hz), 7.5 (1H, s).

IR (KBr) $\nu_{max}$ cm$^{-1}$: 1689, 1615, 1463.

Elementary analysis for $C_{20}H_{21}N_4O_4SF \cdot HCl \cdot 1H_2O$:

Calcd. (%): C,49.33; H,4.97; N,11.51
Found (%): C,49.23; H,4.88; N,11.41.

EXAMPLE 11

Preparation of 9,1-(methylimino)methano 7-fluoro-8-(3-methoxymethyl-4-methyl-1-piperazinyl)-5-oxo-5H-thiazolo[3,2-a]quinoline-4-carboxylic acid hydrochloride [compound (I) in which Z is 3-methoxymethyl-4-methyl-1-piperazinyl, hydrochloride thereof]

A mixture of diacetoxy [9,1-(methylimino)methano-7,8-difluoro-5-oxo-5H-thiazolo[3,2-a]quinoline-4-carboxy]borane (cf. Example 25 hereinafter) (0.63 g), 2-methoxymethyl-1-methylpiperazine dihydrochloride (cf. Reference Example 19) (0.76 g), triethylamine (1.95 ml) and dimethylsulfoxide (12 ml) is stirred at 60° C. for 5 hours. The reaction mixture is concentrated to dryness under reduced pressure, and to the residue is added 2N hydrochloric acid (10 ml) and ethanol (20 ml), and the mixture is stirred under ice cooling for 30 minutes. The precipitated crystal is washed with ethanol and acetone, and then recrystallized from 2N hydrochloric acid to give the title compound (0.4 g).

M.p. decomposed at around 248° C.

NMR ($D_2O$) δ: 2.7 (3H, s), 3.1 (3H, s), 3.5 (3H, s), 3.4–3.8 (6H, m), 3.9–4.1 (1H, m), 4.3 (2H, s), 6.6 (1H, d, J=12Hz), 7.3 (1H, s).

IR (KBr) $\nu_{max}$ cm$^{-1}$: 1680, 1616, 1476.

Elementary analysis for $C_{21}H_{23}N_4O_4SF \cdot HCl \cdot 3/2 H_2O$:

Calcd. (%): C,49.46; H,5.34; N,10.99
Found (%): C,49.48; H,5.43; N,10.97.

EXAMPLE 12

Preparation of 9,1-(methylimino)methano-7-fluoro-8-(3-fluoromethyl-4-methyl-1-piperazinyl)-5-oxo-5H-thiazolo[3,2-a]quinoline-4-carboxylic acid hydrochloride [compound (I) in which Z is 3-fluoromethyl-4-methyl-1-piperazinyl, hydrochloride thereof]

A mixture of diacetoxy [9,1-(methylimino)methano-7,8-difluoro-5-oxo-5H-thiazolo[3,2-a]quinoline-4-carboxyl]-borane (cf. Example 25 hereinafter) (0.19 g), 2-fluoromethyl-1-methylpiperazine dihydrochloride (cf. Reference Example 20) (0.17 g), triethylamine (0.94 ml) and dimethylsulfoxide (5 ml) is stirred at 65° C. for 4 hours. The reaction mixture is concentrated to dryness under reduced pressure, and to the residue is added 2N hydrochloric acid (6 ml), and the mixture is stirred at room temperature for 30 minutes. The reaction mixture is filtered, and the filtrate is evaporated to dryness under reduced pressure. To the residue is added ethanol, and the precipitated crystal is separated by filtration. The crystal is recrystallized from 2N hydrochloric acid-ethanol to give the title compound (72 mg).

M.p. decomposed at around 250° C.

NMR ($D_2O$) δ: 2.8 (3H, s), 3.2 (3H, s), 3.5–4.0 (7H, m), 4.4 (2H, s), 4.7–5.3 (2H, m), 6.9 (1H, d, J=12Hz), 7.4 (1H, s).

IR (KBr) $\nu_{max}$ cm$^{-1}$: 1676, 1616, 1472.

Elemental analysis for $C_{20}H_{20}N_4O_3SF_2 \cdot HCl \cdot 1H_2O$:

Calcd. (%): C,49.13; H,4.74; N,11.46
Found (%): C,49.30; H,4.72; N,11.09.

EXAMPLE 13

Preparation of
9,1-(methylimino)methano-7-fluoro-8-(4-hydroxypiperidino)-5-oxo-5H-thiazolo[3,2-a]quinoline-4-carboxylic acid [compound (I) in which Z is 4-hydroxypiperidino]

A mixture of diacetoxy [9,1-(methylimino)methano-7,8-difluoro-5-oxo-5H-thiazolo[3,2-a]quinoline-4-carboxy]-borane (cf. Example 25 hereinafter) (0.5 g), 4-hydroxypiperidine (0.43 g) and dimethylsulfoxide (5 ml) is stirred at room temperature for 19 hours. The reaction mixture is concentrated to dryness under reduced pressure, and to the residue is added 2N hydrochloric acid (6 ml) and acetone (10 ml), and the mixture is stirred at room temperature for 30 minutes. The precipitated crystal is separated by filtration, washed with water and acetone and then recrystallized from dimethylsulfoxide to give the title compound (0.17 g).

M.p. above 280° C.

NMR (DMSO-$d_6$) δ: 1.5–1.7 (2H, m), 1.8–1.9 (2H, m), 2.8 (3H, s), 3.1–3.3 (2H, m), 3.5–3.6 (2H, m), 3.7 (1H, m), 4.5 (2H, s), 4.8 (1H, d, J=4Hz), 7.5 (1H, s), 7.6 (1H, d, J=12.5Hz), 15.8 (1H, s).

IR (KBr) $\nu_{max}$ cm$^{-1}$: 1693, 1526, 1455.

Elementary analysis for $C_{19}H_{18}N_4O_4SF \cdot H_2O$:
Calcd. (%): C,54.15; H,4.78; N,9.97
Found (%): C,54.23; H,4.80; N,9.77.

EXAMPLE 14

Preparation of
9,1-(methylimino)methano-7-fluoro-8-(2-methylmorpholino)-5-oxo-5H-thiazolo[3,2-a]quinoline-4-carboxylic acid [compound (I) in which Z is 2-methylmorpholino]

9,1-(Methylimino)methano-7,8-difluoro-5-oxo-5H-thiazolo[3,2-a]quinoline-4-carboxylic acid (cf. Reference Example 9) (0.3 g) is added to a mixture of dimethylsulfoxide (3 ml), 2-methylmorpholine hydrochloride (cf. Reference Example 14) (0.15 g) and triethylamine (0.47 g), and the mixture is stirred at 95° C. for 15 hours. Dimethylsulfoxide is distilled off under reduced pressure, and the residue is washed with water, ethanol and diethyl ether in this order and recrystallized from acetonitrile-ethanol to give the title compound (0.18 g). This product is identical with 9,1-(methylimino)methano-7-fluoro-8-(2-methylmorpholino)-5-oxo-5H-thiazolo[3,2-a]quinoline-4-carboxylic acid obtained in Example 1 in the physical properties.

EXAMPLE 15

Preparation of
9,1-(methylimino)methano-7-fluoro-8-(2-fluoromethylmorpholino)-5-oxo-5H-thiazolo[3,2-a]-quinoline-4-carboxylic acid [compound (I) in which Z is 2-fluoromethylmorpholino]

This compound is prepared by the following two steps.

(1) Ethyl 9,1-(methylimino)methano-7-fluoro-8-(2-fluoromethylmorpholino)-5-oxo-5H-thiazolo[3,2-a]quinoline-4-carboxylate:

Ethyl 9,1-(methylimino)methano-7,8-difluoro-5-oxo-5H-thiazolo[3,2-a]quinoline-4-carboxylate (cf. Reference Example 7) (0.5 g), 2-fluoromethylmorpholine hydrochloride (cf. Reference Example 13) (0.28 g) and triethylamine (0.72 g) are added to dimethylsulfoxide (5 ml), and the mixture is stirred at 95° C. for 240 hours.

The reaction mixture is concentrated to dryness under reduced pressure, and to the residue is added water, and the mixture is extracted with chloroform. The chloroform layer is washed with water, dried over anhydrous sodium sulfate and concentrated to dryness under reduced pressure. The resulting residue is purified by medium pressure silica gel column chromatography (eluent, chloroform-methanol=50:1) and recrystallized from ethanol-chloroform to give the title compound (0.16 g).

NMR (CDCl$_3$) δ: 1.5 (3H, t, J=7Hz), 2.8 (3H, s), 3.2–3.6 (4H, m), 3.8–4.1 (3H, m), 4.3 (2H, s), 4.4–4.6 (3H, m), 6.8 (1H, s), 7.9 (1H, d, J=12.5Hz).

(2) 9,1-(Methylimino)methano-7-fluoro-8-(2-fluoromethylmorpholino)-5-oxo-5H-thiazolo[3,2-a]quinoline-4-carboxylic acid:

The above ethyl 9,1-(methylimino)methano-7-fluoro-8-(2-fluoromethylmorpholino)-5-oxo-5H-thiazolo[3,2-a]-quinoline-4-carboxylate (0.1 g) and 1N aqueous sodium hydroxide (1.6 ml) are added to ethanol (50 ml), and the mixture is refluxed for 10 hours. The reaction mixture is concentrated to dryness under reduced pressure, and to the residue is added water, and the mixture is washed with chloroform. The aqueous layer is separated and adjusted to pH 6.8 by adding 3N hydrochloric acid. The precipitated crystal is separated by filtration, dried and then recrystallized from chloroform-ethanol to give the title compound (0.04 g). This product is identical with 9,1-(methylimino)methano-7-fluoro-8-(2-fluoromethylmorpholino)-5-oxo 5H-thiazolo[3,2-a]quinoline-4-carboxylic acid obtained in Example 3 in the physical properties.

EXAMPLE 16

Preparation of
9,1-(methylimino)methano-7-fluoro-8-(2-hydroxymethylmorpholino)-5-oxo-5H-thiazolo[3,2-a]-quinoline-4-carboxylic acid [compound (I) in which Z is 2-hydroxymethylmorpholino]

A mixture of difluoro [9,1-(methylimino)methano-7,8-difluoro-5-oxo-5H-thiazolo[3,2-a]quinoline-4-carboxy]borane (cf. Example 27 hereinafter) (114 g), 2-benzoyloxymethylmorpholine hydrochloride (cf. Reference Example 23) (114 g), triethylamine (157 g) and dimethylsulfoxide (650 ml) is stirred at 70° C. for 24 hours. The precipitated crystal is separated by filtration, washed with water and ethanol in this order, and thereto are added water (1.5 liter), ethanol (1.5 liter) and sodium hydroxide (61 g), and the mixture is stirred at 70° C. for 24 hours. After filtering off the insoluble materials, the filtrate is adjusted to pH 5 with 6N hydrochloric acid, and the precipitated crystal is washed with water and acetone in this order and then recrystallized from dimethylsulfoxide to give the title compound (46 g). This product is identical with 9,1-(methylimino)methano-7-fluoro-8-(2-hydroxymethylmorpholino)-5-oxo-5H-thiazolo[3,2-a]quinoline-4-carboxylic acid obtained in Example 2 in the physical properties.

EXAMPLE 17

Preparation of
9,1-(methylimino)methano-7-fluoro-8-[(2S)-2-hydroxymethylmorpholino)-5-oxo-5H-triazolo[3,2-a]-quinoline-4-carboxylic acid [compound (I) in which Z is (2S)-2-hydroxymethylmorpholino]

To a mixture of difluoro [9,1-(methylimino)methano-7,8-difluoro-5-oxo-5H-thiazolo[3,2-a]quinoline-4-carboxy]borane (cf. Example 27 hereinafter) (0.7 g), (2S)-2-benzoyloxymethylmorpholine hydrochloride (cf. Reference Example 24) (1.0 g) and dimethylsulfoxide (10 ml) is added triethylamine (1.4 ml), and the mixture is stirred at 70° C. for 19 hours. The reaction mixture is added to water (30 ml) and the insoluble materials are separated by filtration and washed with water and acetone. To the insoluble materials are added 2N aqueous sodium hydroxide (10 ml) and ethanol (10 ml), and the mixture is refluxed for 3 hours. The reaction mixture is ice-cooled and made acidic with conc. hydrochloric acid, and the precipitated crystal is separated by filtration, washed with acetone, and then recrystallized from dimethylsulfoxide-ethanol to give the title compound (0.3 g).

M.p decomposed at around 254° C.
NMR (DMSO-$d_6$) δ: 2.8 (3H, s), 3.0–3.1 (1H, m), 3.2–3.8 (7H, m), 3.9–4.0 (1H, m), 4.5 (2H, s), 4.8 (1H, t, J=5.5Hz), 7.5 (1H, d, J=12.5Hz), 7.5 (1H, s), 15.7 (1H, s).
IR (KBr) $\nu_{max}$ cm$^{-1}$: 1690, 1612, 1488, 1476, 1450, 1406.
Elementary analysis for $C_{19}H_{18}N_3O_5SF$:
Calcd. (%): C,54.41; H,4.33; N,10.02
Found (%): C,54.20; H,4.41; N,9.87.
$[\alpha]_D^{21}$ +30.6° (c=0.5, 0.1N NaOH)

EXAMPLE 18

Preparation of 9,1-(methylimino)methano-7-fluoro-8-(2R)-2-hydroxymethylmorpholino)-5-oxo-5H-thiazolo[3,2-a]-quinoline-4-carboxylic acid [compound (I) in which Z is (2R)-2-hydroxymethylmorpholino]

In the same manner as described in Example 17 except that (2R)-2-benzoyloxymethylmorpholine hydrochloride (cf. Reference Example 25) is used instead of (2S)-2-benzoyloxymethylmorpholine hydrochloride, there is prepared the title compound.

M.p. decomposed at around 250° C.
NMR (DMSO-$d_6$) δ: 2.8 (3H, s), 3.0–3.1 (1H, m), 3.2–3.8 (7H, m), 3.9–4.0 (1H, m), 4.5 (2H, s), 4.8 (1H, t, J=5.5Hz), 7.5 (1H, d, J=12.5Hz), 7.5 (1H, s), 15.7 (1H, s).
IR (KBr) $\nu_{max}$ cm$^{-1}$: 1690, 1612, 1488, 1476, 1450, 1406.
Elementary analysis for $C_{19}H_{18}N_3O_5SF$:
Calcd. (%): C,54.41; H,4.33; N,10.02
Found (%): C,54.23; H,4.25; N,9.85.
$[\alpha]_D$ < −29.1° (c=0.5, 0.1N NaOH)

EXAMPLE 19

Preparation of sodium 9,1-(methylimino)methano-7-fluoro-8-[2-hydroxymethylmorpholino)-5-oxo-5H-thiazolo[3,2-a]quinoline-4-carboxylate [compound (I) in which Z is 2-hydroxymethylmorpholino, sodium salt thereof]

9,1-(Methylimino)methano-7-fluoro-8-(2-hydroxymethylmorpholino)-5-oxo-5H-thiazolo[3,2-a]quinoline-4-carboxyic acid (cf. Example 16) (2.2 g) is suspended in water (12.3 ml) and thereto is added 2N aqueous sodium hydroxide (2.7 ml), and the mixture is heated to dissolve it. To the mixture is added 2N aqueous sodium hydroxide (15 ml), and the mixture is allowed to stand at room temperature. The precipitated crystal is separated by filtration and washed with 2N aqueous sodium hydroxide and methanol to give the title compound (1.3 g).

M.p. above 280° C.
NMR (D$_2$O) δ: 2.4 (3H, s), 2.9–3.3 (4H, m), 3.6–4.1 (5H, m), 3.9 (2H, s), 6.9 (1H, s), 7.3 (1H, d, J=13Hz).
IR (KBr) $\nu_{max}$ cm$^{-1}$: 1607, 1569, 1464.
Elementary analysis for $C_{19}H_{17}N_3O_5SFNa.\frac{3}{4}H_2O$:
Calcd. (%): C,50.16; H,4.10; N,9.24
Found (%): C,50.15; H,4.03; N,9.28.

EXAMPLE 20

Preparation of 9,1-(methylimino)methano-7-fluoro-8-(2-methoxymethylmorpholino)-5-oxo-5H-thiazolo[3,2-a]-quinoline-4-carboxylic acid [compound (I) in which Z is 2-methoxymethylmorpholino]

2-Methoxymethylmorpholine (cf. Reference Example 10) (4.0 g) and triethylamine (7.1 g) are dissolved in dimethylsulfoxide (40 ml), and thereto is added difluoro [9,1-(methylimino)methano-7,8-difluoro-5-oxo-5H-thiazolo-[3,2-a]quinoline-4-carboxy]borane (cf. Example 27 hereinafter) (8.6 g), and the mixture is stirred at 60° C. for 20 hours. To the reaction mixture is added ethanol (160 ml), and the mixture is stirred at room temperature. The resulting precipitate is separated by filtration, washed with water and ethanol in this order, and then suspended in a mixture of ethanol (70 ml) and 2N aqueous sodium hydroxide (35 ml). The mixture is stirred at 100° C. for 1.5 hour. The insoluble materials are filtered off, and the filtrate is adjusted to about pH 6 with 2N hydrochloric acid. The precipitated crystal is separated by filtration, washed with water and ethanol in this order, and then recrystallized from dimethylsulfoxide-ethanol. The crystal is suspended in ethanol (25 ml), and the mixture is refluxed for 7 hours, cooled till room temperature, and the crystal insoluble in ethanol is collected to give the title compound (6.5 g).

M.p. decomposed at around 220° C.
NMR (DMSO-$d_6$) δ: 2.8 (3H, s), 3.0–3.1 (1H, m), 3.2–3.5 (5H, m), 3.3 (3H, s), 3.7–3.8 (2H, m), 3.9–4.0 (1H, m), 4.5 (2H, s), 7.5 (1H, d, J=12.5Hz), 7.5 (1H, s), 15.7 (1H, s).
IR (KBr) $\nu_{max}$ cm$^{-1}$: 1694, 1612, 1488.
Elementary analysis for $C_{20}H_{20}N_3O_5SF$:
Calcd. (%): C,55.42; H,4.65; N,9.69
Found (%): C,55.39; H,4.75; N,9.54.

EXAMPLE 21

Preparation of 9,1-(methylimino)methano-7-fluoro-8-[(2S)-2-methoxymethylmorpholino)-5-oxo-5H-thiazolo[3,2-a] -quinoline-4-carboxylic acid [compound (I) in which Z is (2S)-2-methoxymethylmorpholino]

A mixture of difluoro [9,1-(methylimino)methano7,8-difluoro-5-oxo-5H-thiazolo[3,2-a]quinoline-4-carboxy]-borane (cf. Example 27 hereinafter) (2.5 g), (2S)-2-methoxymethylmorpholine hydrochloride (cf. Reference Example 11) (1.7 g), triethylamine (3.5 ml) and dimethylsulfoxide (30 ml) is stirred at 55°–60° C. for 18 hours. The reaction mixture is concentrated under reduced pressure, and thereto is added ethanol (60 ml). The precipitated crystal is separated by filtration, and thereto are added ethanol (20 ml) and 2N aqueous sodium hydroxide (15 ml), and the mixture is stirred at 80° C. for 2 hours. The insoluble materials are filtered off and the filtrate is adjusted to pH 3 with 2N hydrochloric acid. The precipitated crystal is separated by filtration and recrystallized from dimethylsulfoxide-ethanol to give the title compound (1.9 g).

M.p. decomposed at around 220° C.
NMR (DMSO-d6) δ: 2.8 (3H, s), 3.0-3.1 (1H, m), 3.2-3.5 (5H, m), 3.3 (3H, s), 3.7-3.8 (2H, m), 3.9-4.0 (1H, m), 4.5 (2H, s), 7.6 (1H, s), 7.7 (1H, d, J=12.5Hz), 15.9 (1H, s).
IR (KBr) $\nu_{max}$ cm$^{-1}$: 1694, 1614, 1490.
Elementary analysis for $C_{20}H_{20}N_3O_5SF$:
Calcd. (%): C,55.42; H,4.65; N,9.69
Found (%): C,55.24; H,4.67; N,9.57.
$[\alpha]_D^{20}$ +39.5° (c=0.5, 0.1N NaOH).

EXAMPLE 22

Preparation of 9,1-(methylimino)methano-7-fluoro-8-[(2R)-2-methoxymethylmorpholino)-5-oxo-5H-thiazolo[3,2-a]-quinoline-4-carboxylic acid [compound (I) in which Z is (2R)-2-methoxymethylmorpholino]

In the same manner as described in Example 21 except that (2R) 2 methoxymethylmorpholine hydrochloride (cf. Reference Example 12) is used instead of (2S)-2-methoxymethylmorpholine hydrochloride, there is prepared the title compound.
M.p. decomposed at around 220° C.
NMR (DMSO-d6) δ: 2.8 (3H, s), 3.0-3.1 (1H, m), 3.2-3.5 (5H, m), 3.3 (3H, s), 3.7-3.8 (2H, m), 3.9-4.0 (2H, m), 4.5 (2H, s), 7.6 (1H, s), 7.7 (1H, d, J=12.5Hz), 15.9 (1H, s).
IR (KBr) $\nu_{max}$ cm$^{-1}$: 1694, 1614, 1488.
Elementary analysis for $C_{20}H_{20}N_3O_5SF$:
Calcd. (%): C,55.42; H,4.65; N,9.69
Found (%): C,55.47; H,4.72; N,9.66.
$[\alpha]_D^{20}$ -39.9° (c=0.5, 0.1N NaOH).

EXAMPLE 23

Preparation of sodium 9,1-(methylimino)methano-7-fluoro-8-(2-methoxymethylmorpholino)-5-oxo-5H-thiazolo[3,2-a]quinoline-4-carboxylate [compound (I) in which Z is 2-methoxymethylmorpholino, sodium salt thereof]

9,1-(Methylimino)methano-7-fluoro-8-(2-methoxymethylmorpholino)-5-oxo-5H-thiazolo[3,2-a]quinoline-4-carboxylic acid (cf. Example 20) (5.0 g) is suspended in water (20 ml), and thereto is added 2N aqueous sodium hydroxide (5.9 ml), and the mixture is heated to dissolve it. 5N aqueous sodium hydroxide (17 ml) is added to the mixture, and the mixture is cooled to room temperature. The precipitated crystal is separated by filtration and washed with water-acetone (1:1) and acetone in this order to give the title compound (3.0 g).
M.p. above 280° C.
NMR (D2O) δ: 2.5 (3H, s), 2.9-3.3 (4H, m), 3.4 (3H, s), 3.5-3.6 (2H, m), 3.7-4.1 (3H, m), 4.0 (2H, s), 6.9 (1H, s), 7.4 (1H, d, J=13Hz).
IR (KBr) $\nu_{max}$ cm$^{-1}$: 1607, 1569, 1463.
Elementary analysis for $C_{20}H_{19}N_3O_5SFNa \cdot H_2O$:
Calcd. (%): C,50.74; H,4.47; N,8.88
Found (%): C,50.71; H,4.39; N,8.83.

EXAMPLE 24

Preparation of 9,1-(methylimino)methano-7-fluoro-8-(2-ethoxymethylmorpholino)-5-oxo-5H-thiazolo[3,2-a]-quinoline-4-carboxylic acid [compound (I) in which Z is 2-ethoxymethylmorpholino]

A mixture of diacetoxy [9,1-(methylimino)methano-7,8-difluoro-5-oxo-5H-thiazolo[3,2-a]quinoline-4-carboxy]-borane (cf. Example 25 hereinafter) (1.4 g), 2-ethoxymethylmorpholine (cf. Reference Example 22) (0.7 g), triethylamine (1.6 g) and dimethylsulfoxide (40 ml) is stirred at 65° C. for 16 hours. To the reaction mixture is added water, and the insoluble materials are separated by filtration, and thereto are added acetone (25 ml), conc. hydrochloric acid (8 ml) and water (60 ml), and the mixture is stirred at room temperature for 3 hours. The insoluble materials are separated by filtration, washed with acetonitrile, and then recrystallized from dimethylsulfoxide to give the title compound (0.5 g).
M.p. decomposed at around 231° C.
NMR (DMSO-d6) δ: 1.1 (3H, t, J=7Hz), 2.8 (3H, s), 3.0-3.1 (1H, m), 3.2-3.5 (7H, m), 3.7-3.8 (2H, m), 3.9-4.0 (1H, m), 4.5 (2H, s), 7.6 (1H, s), 7.6 (1H, d, J=12.5Hz), 15.8 (1H, s).
IR (KBr) $\nu_{max}$ cm$^{-1}$: 1706, 1614, 1494, 1464.
Elementary analysis for $C_{21}H_{22}N_3O_5SF \cdot \frac{1}{2}H_2O$:
Calcd. (%): C,55.25; H,5.08; N,9.20
Found (%): C,55.29; H,5.05; N,9.23.

EXAMPLE 25

Preparation of diacetoxy [9,1-(methylimino)methano7,8-difluoro-5-oxo-5H-thiazolo[3,2-a]quinoline-4-carboxy]-borane [compound (II-1) in which $R^3$ is methyl]

A mixture of boric acid (0.27 g) and acetic anhydride (3 g) is stirred at 75°-80° C. for 50 minutes to give a solution of triacetoxyborane, and thereto is added ethyl 9,1-(methylimino)methano-7,8-difluoro-5-oxo-5H-thiazolo[3,2-a]quinoline-4-carboxylate (cf. Reference Example 7) (1.0 g), and the mixture is stirred at 100° C. for 40 minutes. The reaction mixture is allowed to stand at room temperature, and the precipitated crystal is separated by filtration, washed with isopropyl ether to give the title compound (1.26 g). This product is recrystallized from acetonitrile to give the title compound having the following physical properties.
M.p. above 285° C.
NMR (DMSO-d6) δ: 1.9 (6H, s), 3.3 (3H, d, J=6Hz), 4.8 (2H, d, J=1Hz), 7.6 (1H, dd, J=7Hz, J=10Hz), 7.9 (1H, t, J=1Hz).
IR (KBr) $\nu_{max}$ cm$^{-1}$: 1718, 1697.
Elementary analysis for $C_{18}H_{13}N_2O_7SF_2B$:
Calcd (%): C,48.02; H,2.91; N,6.22
Found (%): C,47.92; H,3.02; N,6.21.

EXAMPLE 26

Preparation of dipropionyloxy [9,1-(methylimino)-methano-7,8-difluoro-5-oxo-5H-thiazolo[3,2-a]quinoline-4-carboxy]borane [compound (II-1) in which $R^3$ is ethyl]

A mixture of boric acid (1.1 g) and propionic anhydride (8.0 g) is stirred at 75°-80° C. for 50 minutes to give a solution of tripropionyloxyborane, and thereto is added ethyl 9,1-(methylimino)methano-7,8-difluoro-5-oxo-5H-thiazolo[3,2-a]quinoline-4-carboxylate (cf. Reference Example 7) (4.0 g), and the mixture is refluxed with stirring for 40 minutes. The reaction mixture is allowed to stand at room temperature, and the precipitated crystal is separated by filtration, washed with isopropyl ether, and then recrystallized from acetonitrile to give the title compound (5.1 g).
M.p. decomposed at around 256° C.
NMR (DMSO-d6) δ: 0.9 (6H, t, J=7.5Hz), 2.2 (4H, q, J=7.5Hz), 3.3 (3H, s), 4.8 (2H, s), 7.6 (1H, dd, J=10Hz, J=7Hz), 8.0 (1H, s).

IR (KBr) $\nu_{max}$ cm$^{-1}$: 1724, 1702, 1534.
Elementary analysis for $C_{20}H_{17}N_2O_7SF_2B$:
Calcd. (%): C,50.23; H,3.58; N,5.86
Found (%): C,50.21; H,3.62; N,5.92.

EXAMPLE 27

Preparation of difluoro [9,1-(methylimino)methano7,8-difluoro-5-oxo-5H-thiazolo[3,2-a]quinoline-4-carboxy]borane [compound (II-2)]

To diethyl (5-methyl-6,7-difluoro-1H,4H-thiazolo[3,4-a]quinoxalin-1-ylidene)malonate (cf. Reference Example 6) (2.0 g) are added acetic anhydride (6 ml) and borone trifluoride-etherate complex (0.72 ml), and the mixture is stirred at 100° C. for 8 hours. After allowing to cool, the precipitated crystal is separated by filtration, washed with acetic anhydride and isopropyl ether in this order to give the title compound (1.66 g).
M.p. above 280° C.
NMR (DMSO-d$_6$) δ: 3.4 (3H, d, J=6Hz), 4.8 (2H, d, J=1Hz), 7.7 (1H, dd, J=7Hz, J=10Hz), 8.0 (1H, t, J=1Hz).
IR (KBr) $\nu_{max}$ cm$^{-1}$: 1695, 1533, 1494, 1471, 1462, 1410.
Elementary analysis for $C_{14}H_7N_2O_3SF_4B$:
Calcd. (%): C,45.43: H,1.91: N,7.57
Found (%): C,45.41: H,2.15: N,7.56.

EXAMPLE 28

Preparation of difluoro [9,1 (methylimino)methano7,8-difluoro-5-oxo-5H-thiazolo[3,2 a]quinoline 4-carboxy]-borane [compound (I) in which R is difluoroboryl]

Ammonium fluoroborate (1.06 g) is added to acetic anhydride (10 ml), and the mixture is stirred at 100° C. for one hour. To the mixture is added diethyl (5-methyl-6,7-difluoro-1H,4H-thiazolo[3,4-a]quinoxalin-1-ylidene)malonate (cf. Reference Example 6) (2.0 g), and the mixture is stirred at the same temperature as above for 5 hours. The reaction mixture is allowed to stand at room temperature, and the precipitated crystal is separated by filtration, washed with ethyl acetate, water and acetone in this order to give the title compound (1.7 g). This product is identical with difluoro [9,1-(methylimino)methano-7,8-difluoro-5-oxo-5H-thiazolo[3,2-a]quinoline-4-carboxy]borane obtained in Example 27 in the physical properties.

EXAMPLE 29

Preparation of Tablets

Tablets each containing 100 mg of 9,1-(methylimino)-methano-7-fluoro-8-(2-fluoromethylmorpholino)-5-oxo-5H-thiazolo[3,2-a]quionoline-4-carboxylic acid [compound of Example 3] are prepared as follows:

| (Formula) | |
|---|---|
| Ingredients | Part by weight |
| The active ingredient (compound of Example 3) | 100 |
| Corn starch | 46 |
| Microcrystalline cellulose | 98 |
| Hydroxypropyl cellulose | 2 |
| Magnesium stearate | 4 |

(Procedure)

To a mixture of the active ingredient, corn starch and microcrystalline cellulose is added a solution of hydroxypropyl cellulose in water (50 parts by weight) and the mixture is kneaded well. The kneaded mixture is passed through a mesh to produce granules. After drying the granules, magnesium stearate is mixed with the granules and the mixture is tabletted by a conventional method to give tablets (each 250 mg).

EXAMPLE 30

Preparation of Granules

Granules each containing 9,1-(methylimino)methano7-fluoro-8-(2-fluoromethylmorpholino)-5-oxo-5H-thiazolo[3,2-a]quinoline-4-carboxylic acid [compound of Example 3] (200 mg) per 500 mg granules are prepared as follows:

| (Formula) | |
|---|---|
| Ingredients | Part by weight |
| The active ingredient (compound of Example 3) | 200 |
| Lactose | 185 |
| Corn starch | 109 |
| Hydroxypropyl cellulose | 6 |

(Procedure)

To a mixture of the active ingredient, lactose and corn starch is added a solution of hydroxypropyl cellulose in water (120 parts by weight) and the mixture is kneaded well. The kneaded mixture is passed through a No. 20 mesh sieve to produce granules. The granules are dried and passed through a sieve of desired size to yield the granules.

EXAMPLE 31

Preparation of Capsules

Capsules each containing 100 mg of 9,1-(methylimino)methano-7-fluoro-8-(2-fluoromethylmorpholino)-5-oxo-5H-thiazolo[3,2-a]quinoline-4-carboxylic acid [compound of Example 3] are prepared as follows:

| (Formula) | |
|---|---|
| Ingredients | Part by weight |
| The active ingredient (compound of Example 3) | 100 |
| Lactose | 35 |
| Corn starch | 60 |
| Magnesium stearate | 5 |

(Procedure)

All the above ingredients were mixed throughly and the resulting powdery mixture was packed into gelatin capsules in each amount of 200 mg.

EXAMPLES 32-34

Preparation of Tablets

Tablets each containing 100 mg of 9,1-(methylimino)-methano-7-fluoro-8-(2-methylmorpholino)-5-oxo-5H-thiazolo[3,2-a]quinoline-4-carboxylic acid [compound of Example 1], 9,1-(methylimino)methano-7-fluoro-8-(2-hydroxymethylmorpholino)- 5-oxo-5H-thiazolo[3,2-a]quinoline-4-carboxylic acid [compound of Example 2], or 9,1-(methylimino)methano-7-fluoro-8-(2-methoxymethylmorpholino)-5-oxo-5H-thiazolo[3,2-a]quinoline-4-carboxylic acid (compound of Example 20) are prepared by the procedure as described in Example 29 except that the compound of Example 1, 2 or 20 is employed in place of the compound of Example 3 as the active ingredient.

EXAMPLES 35-37

Preparation of Granules

Granules each containing 9,1-(methylimino)methano-7-fluoro-8-(2-methylmorpholino)-5-oxo-5H-thiazolo[3,2-a]-quinoline-4-carboxylic acid hydrochloride [compound of Example 1], 9,1-(methylimino)methano-7-fluoro-8-(2-hydroxymethylmorpholino)-5-oxo-5H-thiazolo[3,2-a]quinoline-4-carboxylic acid [compound of Example 2] or 9,1-(methylimino)methano-7-fluoro-8-(2-methoxymethylmorpholino) 5 oxo-5H-thiazolo[3,2-a]quinoline-4-carboxylic acid [compound of Example 20] is prepared by the procedure as described in Example 30 except that the compound of Example 1, 2 or 20 is employed in place of the compound of Example 3 as the active ingredient.

What is claimed is:

1. A quinolinecarboxylic acid derivative of the formula:

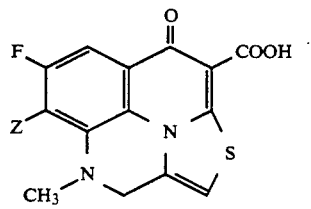

wherein

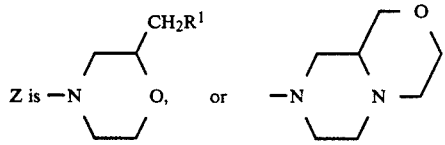

in which R¹ is hydrogen, chlorine, fluorine hydroxy, methoxy or ethoxy, or a pharmaceutically acceptable salt thereof.

2. The compound according to claim 1, wherein Z is

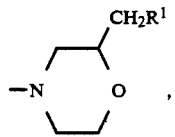

(where R¹ is hydrogen, chlorine, fluorine, hydroxy, methoxy or ethoxy, or a pharmaceutically acceptable salt thereof.

3. The compound according to claim 1, wherein Z is

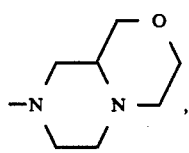

or a pharmaceutically acceptable salt thereof.

4. The compound according to claim 1, which is a member selected from the following compounds:

9,1-(Methylimino)methano-7-fluoro-8-(2-methylmorpholino)-5-oxo-5H-thiazolo[3,2-a]quinoline-4-carboxylic acid, or a pharmaceutically acceptable salt thereof;

9,1-(Methylimino)methano-7-fluoro-8-(2-hydroxymethylmorpholino)-5-oxo-5H-thiazolo[3,2-a]quinoline-4-carboxylic acid, or a pharmaceutically acceptable salt thereof;

9,1-(Methylimino)methano-7-fluoro-8-(2-fluoromethylmorpholino)-5-oxo-5H-thiazolo[3,2-a]quinoline-4-carboxylic acid, or a pharmaceutically acceptable salt thereof;

9,1-(Methylimino)methano-7-fluoro-8-(2-chloromethylmorpholino)-5-oxo-5H-thiazolo[3,2-a]quinoline-4-carboxylic acid, or a pharmaceutically acceptable salt thereof;

9,1-(Methylimino)methano-7-fluoro-8-(2-methoxymethylmorpholino)-5-oxo-5H-thiazolo[3,2-a]quinoline-4-carboxylic acid, or a pharmaceutically acceptable salt thereof;

9,1-(Methylimino)methano-7-fluoro-8-[(6R)-1,8-diaza-4-oxabicyclo[4.4.0]deca-8-yl]-5-oxo-5H-thiazolo[3,2-a]quinoline-4-carboxylic acid, or a pharmaceutically acceptable salt thereof;

9,1-(Methylimino)methano-7-fluoro-8-[(2S)-2-hydroxymethylmorpholino]-5-oxo-5H-thiazolo[3,2-a]quinoline-4-carboxylic acid, or a pharmaceutically acceptable salt thereof;

9,1-(Methylimino)methano-7-fluoro-8-[(2R)-2-hydroxymethylmorpholino]-5-oxo-5H-thiazolo[3,2-a]quinoline-4-carboxylic acid, or a pharmaceutically acceptable salt thereof;

9,1-(Methylimino)methano-7-fluoro-8-[(2S)-2-methoxymethylmorpholino]-5-oxo-5H-thiazolo[3,2-a]quinoline-4-carboxylic acid, or a pharmaceutically acceptable salt thereof;

9,1-(Methylimino)methano-7-fluoro-8-[(2R)-2-methoxymethylmorpholino]-5-oxo-5H-thiazolo[3,2-a]quinoline-4-carboxylic acid, or a pharmaceutically acceptable salt thereof;

9,1-(Methylimino)methano-7-fluoro-8-(2-ethoxymethylmorpholino)-5-oxo-5H-thiazolo[3,2-a]quinoline-4-carboxylic acid, or a pharmaceutically acceptable salt thereof.

5. An antibacterial composition comprising as an active ingredient an effective amount of a quinolinecarboxylic acid derivative of the formula:

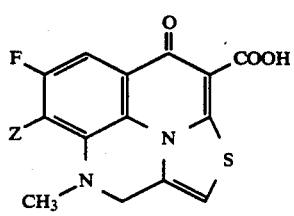

wherein

Z is 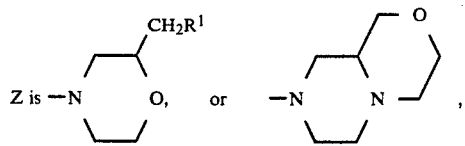

in which R¹ is hydrogen, chlorine, fluorine, hydroxy, methoxy or ethoxy, or a pharmaceutically acceptable salt thereof, in admixture with pharmaceutically acceptable carrier or diluent.

6. The composition of claim 5, which is in a form for oral administration.

7. A method for providing an antibacterial effect to a subject need thereof, comprising administering to the subject an antibacterially-effective amount of a compound according to claim 1 or a pharmaceutically acceptable salt thereof.

8. The method of claim 7, wherein the compound is administered orally.

* * * * *

UNITED STATES PATENT AND TRADEMARK OFFICE
CERTIFICATE OF CORRECTION

PATENT NO. : 5,166,203

DATED : November 24, 1992

INVENTOR(S) : Hirosato KONDO et al.

It is certified that error appears in the above-identified patent and that said Letters Patent is hereby corrected as shown below:

On title page,

Item 22: Change "May 12, 1991" to --May 21, 1991--.

Item 75: Change "Hirosata Kondo" to --Hirosato Kondo--.

Col. 55, claim 2, line 57, change "...ethoxy, or..." to --...ethoxy),or ...--

Signed and Sealed this

Seventh Day of December, 1993

Attest:

BRUCE LEHMAN

Attesting Officer     Commissioner of Patents and Trademarks